US008889921B2

(12) United States Patent
Greenfield

(10) Patent No.: US 8,889,921 B2
(45) Date of Patent: Nov. 18, 2014

(54) METHODS OF SYNTHESIS OF SCYLLITOL AND RELATED COMPOUNDS

(75) Inventor: Scott Greenfield, Delmar, NY (US)

(73) Assignee: Transition Therapeutics Ireland Limited, Dublin (IE)

( * ) Notice: Subject to any disclaimer, the term of this patent is extended or adjusted under 35 U.S.C. 154(b) by 203 days.

(21) Appl. No.: 13/273,069

(22) Filed: Oct. 13, 2011

(65) Prior Publication Data

US 2012/0116130 A1    May 10, 2012

Related U.S. Application Data

(60) Provisional application No. 61/455,089, filed on Oct. 13, 2010.

(51) Int. Cl.
| | |
|---|---|
| *C07C 35/14* | (2006.01) |
| *C07C 29/12* | (2006.01) |
| *C07C 29/92* | (2006.01) |
| *C07C 29/56* | (2006.01) |
| *C07C 29/78* | (2006.01) |

(52) U.S. Cl.
CPC .............. *C07C 29/12* (2013.01); *C07C 29/92* (2013.01); *C07C 29/56* (2013.01); *C07C 2101/14* (2013.01); *C07C 29/78* (2013.01)
USPC ........................................................ 568/833

(58) Field of Classification Search
None
See application file for complete search history.

(56) References Cited

U.S. PATENT DOCUMENTS

| | | | |
|---|---|---|---|
| 3,627,636 A | 12/1971 | Jaffe et al. | |
| 5,412,080 A | 5/1995 | Kishi et al. | |
| 5,997,881 A | 12/1999 | Powell et al. | |
| 7,037,378 B2 | 5/2006 | Jumppanen et al. | |
| 7,745,671 B2 | 6/2010 | Yamaguchi et al. | |
| 8,409,833 B2 | 4/2013 | Yamaguchi et al. | |

(Continued)

FOREIGN PATENT DOCUMENTS

| | | |
|---|---|---|
| DE | 3405663 A1 | 8/1985 |
| DE | 4231063 | 3/1994 |

(Continued)

OTHER PUBLICATIONS

Anderson et al., "The Catalytic Hydrogenation of Polyhydric Phenols. I. The Synthesis of meso-Inositol, Scyllitol and a New Isomeric Cyclitol", *J. American. Chem. Soc.* 70 (9), 2931-2935 (1948).

(Continued)

*Primary Examiner* — Karl J Puttlitz
(74) *Attorney, Agent, or Firm* — Millen, White, Zelano & Branigan, PC

(57) ABSTRACT

Methods of synthesis of scyllitol diborate and related compounds are provided, including methods that are performed in all-aqueous solutions. Also provided are methods in which the reaction products are recycled to increase the efficiency of the process. The methods include the steps of conversion of a solution of inositol to scyllitol, conversion of scyllitol in the solution to scyllitol diborate, and isolation of the scyllitol diborate from the solution. The scyllitol diborate is reacted to form substantially pure scyllitol diborate, and the remaining solution is efficiently recycled to scyllitol diborate, then to additional substantially pure scyllitol. This scyllitol diborate recycling step can be applied to a variety of processes to improve the yield of scyllitol. The methods are highly efficient and result in large scale reaction products of high purity.

24 Claims, 4 Drawing Sheets

(56) References Cited

U.S. PATENT DOCUMENTS

| | | | |
|---|---|---|---|
| 2006/0240534 | A1 | 10/2006 | Yamaguchi et al. |
| 2006/0257981 | A1 | 11/2006 | Shue et al. |
| 2007/0112187 | A1 | 5/2007 | Heikkila et al. |
| 2007/0196556 | A1 | 8/2007 | Van Der Meer |
| 2008/0044861 | A1 | 2/2008 | Weber et al. |
| 2008/0060638 | A1 | 3/2008 | Koivikko et al. |
| 2009/0036576 | A1 | 2/2009 | Elbahloul et al. |
| 2010/0261238 | A1 | 10/2010 | Yamaguchi et al. |
| 2011/0201060 | A1* | 8/2011 | Reddy et al. .................. 435/105 |
| 2013/0196417 | A1 | 8/2013 | Yamaguchi et al. |

FOREIGN PATENT DOCUMENTS

| | | | |
|---|---|---|---|
| EP | 1674578 | * | 6/2006 |
| EP | 1674578 | A1 | 6/2006 |
| WO | WO 2004/075882 | A1 | 9/2004 |
| WO | WO2005035774 | | 4/2005 |
| WO | WO 2007/041855 | A1 | 4/2007 |
| WO | WO 2007/119108 | A2 | 10/2007 |
| WO | WO 2011/100670 | A1 | 8/2011 |

OTHER PUBLICATIONS

Husson et al., "New conditions for the synthesis of scyllo-inositol starting from myo-inositol", *Carbohydrate Research*, vol. 307, (1-2), 163-165 (1998).

Kiely et al., "Cyclization of D-xylo-hexos-5-ulose, a chemical model for the biosynthesis of myo- and scyllo-inositols", *J. American Chem. Soc.* 90 (12), 3289-3290 (1968).

McLaurin et al., "Inositol Stereoisomers Stabilize an Oligomeric Aggregate of Alzheimer Amyloid β Peptide and Inhibit Aβ-induced Toxicity", J. Biol. Chem., 275, 18495-18502 (2000).

Patent Cooperation Treaty, International Searching Authority, Search Report and Written Opinion for PCT/US2011/056109, 10 pages, Mar. 5, 2012.

Takahashi, Hideyo et al., "Novel Synthesis of Enantiomerically Pure Natural Inositols and Their Diastereoisomers", *Journal of Organic Chemistry*, vol. 66 (8), 2705-2716 (2001).

Vogl et al., "Synthesis of Hexaoxadiamantanes", *Journal of Organic Chemistry*, vol. 34 (1), 204-207 (1969).

Weissbach, "Scyllitol Diborate", *J. Org. Chem.*, 23 (2), 329-330 (1958).

Angyal, S. J. et al., "Cyclitols. Part VI. The Hydrogenation of Hexahydroxy-benzene," J. Chem. Soc., 1957, pp. 3682-3691.

Cousins, G. et al., "Monoesterification of di-O-isopropylidene and di-O-cyclohexylidene chiro-inositols," Carbohydrate Research, 2003, vol. 338, pp. 995-998.

Ghias-Ud-Din, M. et al., "Separation of pinitol and some other cyclitols by high-performance liquid chromatography," Journal of Chromatography, 1981, vol. 211, vol. 295-298.

Grainger, C. T. et al., "The structure of Sodium scyllo-Inositol Diborate Decahydrate," Acta Cryst., 1981, vol. B37, pp. 563-568.

International Search Report for PCT/US2011/024731 dated Apr. 25, 2011.

Kiely, D. E. et al., "Cyclization of D-xylo-Hexos-5-ulose, a Chemical Synthesis of Scyllo- and myo-Inositols from D-Glucose," The Journal of Organic Chemistry, May 1969, pp. 1386-1390.

Kluyver, A. J. et al. "Note on the biochemical preparation of inosose," Recueil des Travaux Chimiques des Pays-Bas, 1939, vol. 58, No. 11, pp. 956-958.

Lampe, D. et al, "Synthesis of L-scyllo-inositol 1,2,4-trisphosphate, scyllo-inositol 1,2,4,5-tetrakisphosphate and phosphorothioate and DL-2-deoxy-2-fluoro-myo-inositol 1,4,5-trisphosphate: optical resolution of DL-1-O-allyl-3,6-di-O-benzyl-4,5-O-isopropylidene-scyllo-inositol," J. Am. Chem. Soc. Perkin. Trans. 1, 1996, pp. 1717-1727.

McLaurin, J. et al., "Phosphatidylinositol and Inositol involvement in Alzheimer Amyloid-Beta Fibril Growth and Arrest," J. Mol. Biol. 1998, vol. 278, pp. 183-184.

Michaelis, T. et al., "Identification of Scyllo-Inositol in Proton NMR Spectra of Human Brain in Vivo," NMR in Biomedicine, 1993, vol. 6, pp. 105-109.

Podeschwa, M. et al., "Stereoselective synthesis of myo-, neo-, L-chiro, D-chiro, allo-scyllo-, and epi-Inositol Systems via Conduritols Prepared from p-Benzoquinone," Eur. J. Org. Chem., 2003, pp. 1958-1972.

Sanz, M. L. et al., "Inositols and carbohydrates in different fresh fruit juices," Food Chemistry, 2004, vol. 87, pp. 325-328.

Sasaki, K. et al., "Preparative-scale separation by anion-exchange chromatography of six per-c-deuterated inositol epimers produced during C—1H—C—2H Exchange Reactions with Raney Nickel in Deuterium Oxide," Carbohydrate Research, 1987, vol. 166, pp. 171-180.

Sasaki, K. et al., "Separate of eight inositol isomers by liquid chromatrography under pressure using a calcium-form, cation-exchange column," Carbohydrate Research, 1988, vol. 183, pp. 1-9.

Sherman, W. R. et al., "The identification of myo-Inosose-2 and scyllo-Inositol in Mammalian Tissues," Biochemistry, Feb. 1968, vol. 7, No. 2, pp. 819-824.

Wolfson, W. et al., "Unraveling the tangled brain of Alzheimer's," Chemistry and Biology, Feb. 2008, vol. 15, pp. 89-90.

English Abstract of DE4231063, Publication Date: Mar. 24, 1994.

* cited by examiner

METHODS OF SYNTHESIS OF SCYLLITOL AND RELATED COMPOUNDS

CROSS REFERENCE TO RELATED APPLICATIONS

This application claims priority to U.S. Provisional Application No. 61/455,089 entitled "Methods of Synthesis of Scyllitol and Related Compounds" filed Oct. 13, 2010, which is incorporated herein by reference in its entirety.

BACKGROUND OF INVENTION

Inositol is a cyclohexane modified at each carbon center by a hydroxyl group:

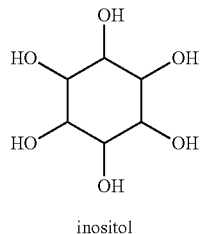

inositol

The compound therefore exists in nine possible stereoisomeric forms:

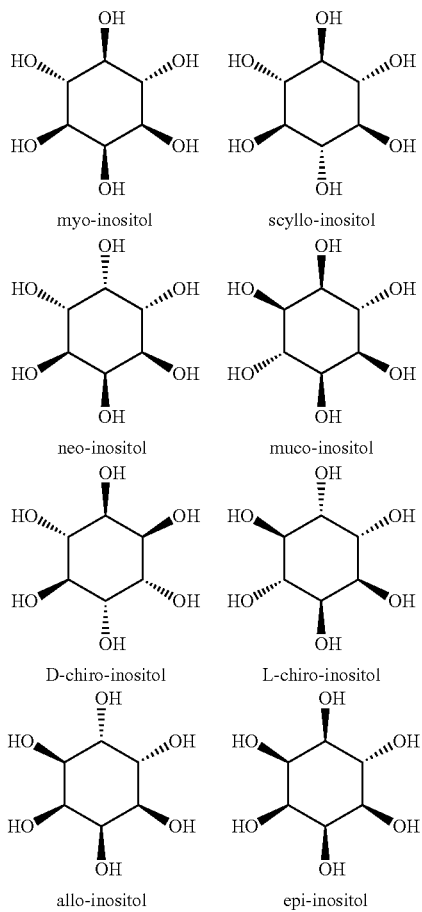

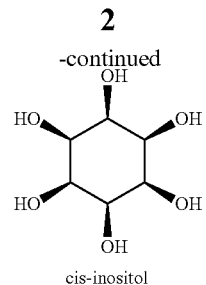

cis-inositol

Of the possible stereoisomers, myo-inositol is the form that occurs most widely in nature. It is a structural component of biologically important compounds that function to generate second messengers in eukaryotes, such as, for example, phosphatidylinositol (PI) and phosphorylated derivatives of PI.

scyllo-Inositol (also known as scyllitol) is also known to occur in nature. In its most stable conformation, scyllitol may be represented as a chair with hydroxyl groups in the six equatorial positions:

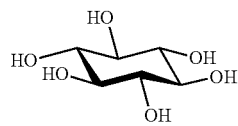

The use of inositol stereoisomers in methods of preventing, treating, and diagnosing disorders of protein folding or aggregation have been reported. See, e.g., PCT International Publication No. WO2004/075882; McLaurin et al. (2000) *J. Biol. Chem.* 275:18495. These methods may therefore prove useful in the prevention, treatment, and diagnosis of amyloidoses such as, for example, Alzheimer's disease. Scyllitol has been used in human clinical trials for the treatment of Alzheimer's disease. See also PCT International Publication Nos. WO2007/041855 and WO2007/119108. The availability of chemically pure stereoisomers of inositol in significant chemical quantities is therefore of critical importance in the development of effective therapeutics in these areas.

The synthesis of scyllitol by chemical, enzymatic, and microbial methods has been reported. For example, Anderson et al. (1948) *J. American Chem. Soc.* 70:2931 describe the formation of inositol stereoisomers, including scyllitol, by the Raney nickel-catalyzed hydrogenation of hexahydroxybenzene.

Kiely et al. (1968) *J. American Chem. Soc.* 90:3289 describe a multi-step chemical synthesis of scyllitol starting from 3-O-benzyl-1,2-O-isopropylidene-6-β-triphenylmethyl-α-D-glucofuranose.

DE3405663 describes a process for the preparation of scyllo-inositol from myo-inositol via myo-inosose, in which the mixture obtained after the oxidation is subjected to an esterification reaction in which a well-crystallizing ester of myo-inosose is formed. The ester is then converted into scyllo-inositol by reduction and hydrolysis.

The process for conversion of myo-inositol to scyllo-inositol can be an enzymatic process, for example a bio-conversion process. European Patent Application Publication No. EP 1 674 578 A1, describes an $NAD^+$-independent enzyme for converting myo-inositol into scyllo-inosose and another enzyme that stereospecially reduces scyllo-inosose into scyllitol. This reference also describes a microorganism that reportedly converts myo-inositol into scyllo-inositol. The disclosure of EP 1 674 578 A1 is incorporated herein by reference as it relates to this process. PCT publication number WO 2011/100670 describes a similar bio-conversion of myo-inositol into scyllo-inosose and scyllo-inositol, the disclosure of which is incorporated herein by reference as it relates to this process.

Husson et al. (1998) *J. American Chem. Soc.* 307:163-165 describes the equilibration of diasteroisomers of sugars by Raney nickel, wherein myo-inositol in water is refluxed with Raney nickel to form a mixture of inositols containing 20-30% of scyllo-inositol.

Reagents useful in the complexation and purification of scyllitol have also been reported. For example, Weissbach (1958) J. Org. Chem. 23:329 describes the formation of scyllitol diborate during the course of reduction of scyllo-myo-inosose with sodium borohydride.

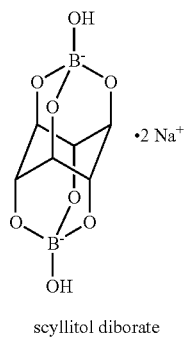 [SMILES: O[B-]12OC3C4O[B-]5(O)OC3C(O1)C(O5)C4O2]

scyllitol diborate

Scyllitol diborate precipitates from the solution as a white solid and could be washed with small amounts of water. According to Weissbach, the compound could also be generated by heating scyllitol in an aqueous borate solution at 100° C.

Vogl et al. (1969) J. Org. Chem. 34:204 also reported the synthesis and characterization of scyllitol diborate. In their method, myo-inositol was biologically oxidized to myo-inosose-2, which was then reduced using sodium borohydride to yield a mixture of borate complexes of scyllitol and myo-inositol. These complexes could be separated due to differences in their solubility. Scyllitol diborate was then converted to scyllitol by treatment with sulfuric acid and methanol. According to Vogl et al., attempts to isomerize myo-inositol directly to scyllitol were unsuccessful.

The above-described methods to synthesize scyllitol either involve inefficient multi-step chemical routes that typically rely on the use of toxic organic solvents or require enzymatic or microbial steps that make large scale production of scyllitol challenging. There is thus a need for improved methods of synthesis of scyllitol and its derivatives.

SUMMARY OF THE INVENTION

The present invention addresses these and other problems by providing novel methods in the preparation of scyllitol and related compounds. In particular, the methods are directed to a large scale process, and are suitable for the large scale production of scyllitol for use in humans.

In a first aspect, a method is provided for preparing substantially pure scyllitol comprising the steps of:
a) subjecting a suitable starting material to a process that results in a mixture comprising scyllitol;
b) conversion of scyllitol in the mixture to scyllitol diborate; and
c) isolation of the scyllitol diborate from the mixture.

In some embodiments of the first aspect, the method further comprises the steps of conversion of isolated scyllitol diborate to scyllitol, and isolation of the scyllitol as substantially pure scyllitol.

In some embodiments of the first aspect, the suitable starting material is inositol. In one embodiment, the inositol comprises myo-inositol, preferably wherein the inositol is myo-inositol.

In some embodiments of the first aspect, the process that results in a mixture comprising scyllitol is the non-specific stereoisomerization of a solution of inositol. In one embodiment, the inositol comprises myo-inositol, preferably wherein the inositol is myo-inositol.

In some embodiments of the first aspect, the process that results in a mixture comprising scyllitol is the reduction of a solution of hexahydroxybenzene with Raney nickel.

In some embodiments of the first aspect, the process that results in a mixture comprising scyllitol is a bioconversion process, wherein a solution of myo-inositol is converted to scyllitol. In some embodiments, the bioconversion process also produces scyllo-inosose. In one embodiment, the process further comprises reacting the scyllo-inosose to form additional scyllitol.

In some embodiments of the first aspect, the solution is an aqueous solution.

In some embodiments of the first aspect, the solution contains no added organic solvent.

In some embodiments of the first aspect, the steps of the method are repeated on the solution following isolation of the scyllitol diborate. In preferred embodiments, the steps of the method are repeated at least 1, 2, 3, 4, 5, 6, 8, 10, or 15 times.

In some embodiments of the first aspect, inositol is added to the solution following isolation of the scyllitol diborate and prior to repeating the steps of the method.

In some embodiments of the first aspect, the stereoisomerization step is mediated by a catalyst. In preferred embodiments, the catalyst is sponge nickel.

In some embodiments of the first aspect, the catalyst is removed prior to the conversion of scyllitol to scyllitol diborate.

In some embodiments of the first aspect, the stereoisomerization step is performed at high temperature.

In some embodiments of the first aspect, the stereoisomerization step is performed at pH 8-9.

In some embodiments of the first aspect, the inositol is myo-inositol.

In some embodiments of the first aspect, the conversion of scyllitol to scyllitol diborate comprises reaction with sodium tetraborate. In some embodiments, the conversion of scyllitol to scyllitol diborate comprises reaction with boric acid.

In some embodiments of the first aspect, the conversion of scyllitol to scyllitol diborate is performed at high temperature.

In certain embodiments of the first aspect, the isolation step comprises filtration.

In certain embodiments, the isolated scyllitol diborate is dried at high temperature.

In some embodiments of the first aspect, the overall yield of scyllitol diborate is at least 20%, 25%, 30%, 35%, or 40%. In a preferred embodiment of the first aspect, the method is a large scale process, for example, the process results in greater than about 1 kg, also about 2 kg, also about 5 kg, also about 10 kg, also about 50 kg, also about 100 kg, preferably greater than about 200 kg, also greater than about 500 kg, also about 1000 kg, also about 5000 kg, also about 10000 kg, also about 12000 kg of substantially pure scyllitol diborate. In some embodiments, the process results in about 1-12000 kg, also about 10-12000 kg, also about 50-12000 kg, also about 50-5000 kg, also about 50-3000 kg, also about 50-1000 kg, also about 50-500 kg, preferably about 50-300 kg of substantially pure scyllitol diborate. In some embodiments, these amounts are obtained from one batch, i.e. step a) is performed once with the suitable starting material, as described in the first aspect. In some embodiments, one or more additional batches can be combined with a first batch to provide a lot of substantially pure scyllitol diborate.

In some embodiments of the first aspect, the conversion of isolated scyllitol diborate to scyllitol comprises a hydrolysis reaction. In specific embodiments, the hydrolysis reaction is mediated by a catalyst. In more specific embodiments, the catalyst is an acid, for example hydrochloric acid, sulfuric acid, nitric acid or phosphoric acid. In even more specific embodiments, the acid is sulfuric acid or hydrochloric acid, preferably hydrochloric acid.

In some embodiments of the first aspect, the conversion of isolated scyllitol diborate to scyllitol is performed at high temperature.

In some embodiments of the first aspect, the conversion of isolated scyllitol diborate to scyllitol is monitored by measurement of pH.

In certain embodiments of the first aspect, the methods further comprise isolation of the scyllitol produced by conversion of isolated scyllitol diborate. In specific embodiments, the scyllitol produced by conversion of isolated scyllitol diborate is isolated by crystallization as substantially pure scyllitol. In even more specific embodiments, the crystallized scyllitol is washed.

In some embodiments of the first aspect, the overall yield of substantially pure scyllitol is at least 20%, 25%, 30%, 35%, or 40%. In a preferred embodiment of the first aspect, the method is a large scale process, for example, the process results in greater than about 1 kg, also about 2 kg, also about 5 kg, also about 10 kg, also about 50 kg, preferably greater than about 100 kg, also greater than about 200 kg, also about 500 kg, also about 1000 kg, also about 5000 kg, also about 8000 kg, also about 10000 kg, also about 14000 kg of substantially pure scyllitol. In some embodiments, the process results in about 1-14000 kg, also about 1-10000 kg, also about 1-8000 kg, also about 1-5000 kg, also about 10-14000 kg, also about 10-8000 kg, also about 50-14000 kg, also about 50-10000 kg, also about 50-8000 kg, also about 50-5000 kg, also about 50-3000 kg, also about 50-1000 kg, also about 50-500 kg, preferably about 50-200 kg of substantially pure scyllitol. In some embodiments, these amounts are obtained from one batch, i.e. step a) is performed once with the suitable starting material, as described in the first aspect. In some embodiments, one or more additional batches can be combined with a first batch to provide a lot of substantially pure scyllitol.

In some embodiments of the first aspect, the scyllitol produced by conversion of isolated scyllitol diborate contains no more than 3 ppm nickel.

In some embodiments of the first aspect, the scyllitol produced by conversion of isolated scyllitol diborate contains no more than 5 ppm aluminum.

In some embodiments of the first aspect, the scyllitol produced by conversion of isolated scyllitol diborate contains no more than 60 ppm boron.

In a second aspect, a method of preparing substantially pure scyllitol is provided comprising the steps of:
  a) non-specific stereoisomerization of a solution of inositol to provide a first mixture comprising scyllitol;
  b) conversion of scyllitol in the first mixture to scyllitol diborate;
  c) isolation of the scyllitol diborate from the first mixture;
  d) conversion of the isolated scyllitol diborate to scyllitol to provide a second mixture comprising scyllitol; and
  e) isolation of substantially pure scyllitol from the second mixture.

In some embodiments of the second aspect, step c) results in a first inositol recovery solution, further comprising repeating steps a) through e) using the first inositol recovery solution in step a).

In some embodiments of the second aspect, the repeat of steps a) through c) results in a second inositol recovery solution, further comprising repeating steps a) through e) using the second inositol recovery solution in step a). In some embodiments, additional inositol is added to the first inositol recovery solution prior to repeating the steps a) through e).

In some embodiments of the second aspect, additional inositol is added to the second inositol recovery solution prior to repeating the steps a) through e).

In some embodiments of the second aspect, step e) comprises filtration.

In some embodiments of the second aspect, step e) results in a diborate recovery solution, further comprising recycling of the diborate recovery solution. In some embodiments said recycling comprises the step of: f) conversion of the diborate recovery solution to recovered scyllitol diborate. In some embodiments said recycling further comprises the step of: g) isolation of the recovered scyllitol diborate. In some embodiments, said recycling further comprises the step of: h) conversion of the isolated recovered scyllitol diborate to scyllitol to form a third mixture comprising scyllitol. In one embodiment said recycling further comprises the step of: i) isolation of the scyllitol from step h) as substantially pure scyllitol.

In some embodiments of the second aspect, the method further comprises recycling of the diborate recovery solution resulting from isolation of the substantially pure scyllitol in step i). In some embodiments the recycling of subsequent diborate recovery solution(s) 1, 2, 3, 4, 5, 6, 7, 8, 9, or 10 times.

In some embodiments of the second aspect, step a) is mediated by a catalyst. In some embodiments, the catalyst is sponge nickel. In some embodiments, the catalyst is removed prior to step b). In some embodiments the catalyst is removed by filtration. In some embodiments, this filtration is performed at high temperature, such as at a temperature in the range of about 50-95° C., preferably in the range of about 70-95° C.

In some embodiments of the second aspect, step a) is performed at high temperature, such as at a temperature in the range of about 90-100° C.

In some embodiments of the second aspect, step a) is performed in aqueous base. In one embodiment step a) is performed at a pH in the range of about 8-12.

In some embodiments of the second aspect, the inositol is myo-inositol.

In some embodiments of the second aspect, step b) comprises reaction with sodium tetraborate. In some embodiments reaction with sodium tatraborate is performed at high temperature, such as at a temperature in the range of about 75-95° C., preferably at a temperature in the range of about 80-90° C. In some embodiments reaction with sodium tatraborate is performed at a pH in the range of about 8-11, preferably in the range of about 9-10. In some embodiments, step b) comprises adding base, preferably NaOH, to bring the mixture to a pH within the range of about 8-11, preferably about 9-10. In a preferred embodiment, reaction with sodium tatraborate is performed at a temperature in the range of about 80-90° C. and a pH in the range of about 9-10.

In some embodiments of the second aspect, step b) comprises reaction with boric acid. In some embodiments reaction with boric acid is performed at high temperature, such as at a temperature in the range of about 75-95° C., preferably at a temperature in the range of about 80-90° C. In some embodiments reaction with boric acid is performed at a pH in the range of about 8-11, preferably in the range of about 9-10. In some embodiments, step b) comprises adding base, preferably NaOH, to bring the mixture to a pH within the range of about 8-11, preferably about 9-10. In a preferred embodiment, reaction with boric acid is performed at a temperature in the range of about 80-90° C. and a pH in the range of about 9-10.

In some embodiments of the second aspect, step b) comprises precipitating scyllitol diborate. In some embodiments, step b) comprises cooling the mixture, preferably to a temperature in the range of 20-30° C. In some embodiments, step b) further comprises agitating the mixture at about 20-30° C. to provide a slurry.

In some embodiments of the second aspect, step c) comprises filtration.

In some embodiments of the second aspect, step d) comprises a hydrolysis reaction. In some embodiments, the hydrolysis reaction is mediated by a catalyst. In some embodiments the catalyst is an acid, such as hydrochloric acid, sulfuric acid, nitric acid or phosphoric acid, preferably sulfuric acid or hydrochloric acid, preferably hydrochloric acid. In some embodiments, the hydrolysis reaction is performed in an aqueous acidic solution, preferably wherein the aqueous acidic solution is about 1N acid, preferably 1N HCl. In some embodiments, the hydrolysis reaction comprises combining isolated scyllitol diborate with about 8-12 volumes of aqueous acid. In some embodiments, the hydrolysis reaction comprises combining isolated scyllitol diborate with about 10 volumes of about 1N acid, preferably 1N HCl. In some embodiments, the hydrolysis reaction is performed at high temperature, such as at a temperature in the range of about 75-95° C., preferably in the range of about 85-95° C.

In some embodiments of the second aspect, step d) is monitored by measurement of pH of the mixture. In some embodiments, step d) is complete when the reaction is at a pH of less than 2.0.

In some embodiments of the second aspect, step d) comprises precipitation of scyllitol in the second mixture. In some embodiments, the precipitation comprises cooling of the second mixture, such as cooling to a temperature in the range of about 20-30° C. In some embodiments, step d) further comprises agitation of the cooled mixture, preferably at 20-30° C. to provide a slurry.

In some embodiments of the second aspect, step e) comprises filtration.

In some embodiments of the second aspect, step f) comprises reaction of the diborate recovery solution in a basic aqueous reaction mixture. In some embodiments, the basic aqueous reaction mixture is reacted at high temperature, such as at a temperature in the range of about 80-90° C. In some embodiments, step f) comprises addition of base to the diborate recovery solution, preferably wherein base is added until the reaction mixture is at a pH in the range of about 9-10. In some embodiments, the added base is NaOH. In some embodiments, step f) further comprises precipitation of the recovered scyllitol diborate from the reaction mixture, preferably wherein precipitation comprises cooling the reaction mixture, preferably cooling to a temperature in the range of about 20-30° C. In some embodiments, step f) further comprises agitation of the reaction mixture at about 20-30° C. to provide a slurry.

In some embodiments of the second aspect, step g) comprises filtration.

In some embodiments of the second aspect, step h) comprises a hydrolysis reaction. In some embodiments, the hydrolysis reaction is mediated by a catalyst, preferably wherein the catalyst is an acid, such as hydrochloric acid, sulfuric acid, nitric acid or phosphoric acid, preferably sulfuric acid or hydrochloric acid, preferably hydrochloric acid. In some embodiments, the hydrolysis reaction is performed in an aqueous acidic solution, preferably wherein the acidic solution is about 1N acid, preferably 1N HCl.

In some embodiments of the second aspect, the hydrolysis reaction of step h) comprises combining isolated recovered scyllitol diborate with about 8-12 volumes of aqueous acid, preferably about 10 volumes of about 1N acid, preferably 1N HCl.

In some embodiments of the second aspect, the hydrolysis reaction of step h) is performed at high temperature, preferably at a temperature in the range of about 85-95° C.

In some embodiments of the second aspect, step h) comprises precipitation of scyllitol in the third mixture. In one embodiment the precipitation comprises cooling of the third mixture, preferably to a temperature in the range of about 20-30° C. In one embodiment, step h) further comprises agitation of the third mixture at about 20-30° C. to provide a slurry.

In some embodiments of the second aspect, step i) comprises filtration.

In a preferred embodiment of the second aspect, the method is a large scale process, for example, the process results in greater than about 1 kg, also about 2 kg, also about 5 kg, also about 10 kg, also about 50 kg, preferably greater than about 100 kg, also greater than about 200 kg, also about 500 kg, also about 1000 kg, also about 5000 kg, also about 8000 kg, also about 10000 kg, also about 14000 kg of substantially pure scyllitol. In some embodiments, the process results in about 1-14000 kg, also about 1-10000 kg, also about 1-8000 kg, also about 1-5000 kg, also about 10-14000 kg, also about 10-8000 kg, also about 50-14000 kg, also about 50-10000 kg, also about 50-8000 kg, also about 50-5000 kg, also about 50-3000 kg, also about 50-1000 kg, also about 50-500 kg, preferably about 50-200 kg of substantially pure scyllitol. In some embodiments, these amounts are obtained from one batch, i.e. step a) is performed once with inositol (i.e. initial use of inositol in step a), inositol recovery solution may be optionally further combined with additional inositol and processed according to the method of step a) as part of a first batch, as described in the second aspect). In some embodiments, one or more additional batches can be combined with a first batch to provide a commercial lot of substantially pure scyllitol.

In a third aspect, a method of preparing substantially pure scyllitol is provided comprising the steps of:
 a) conversion of scyllitol diborate to scyllitol, thereby forming a first scyllitol mixture;
 b) isolation of the scyllitol as a solid from the first scyllitol mixture to provide a first amount of substantially pure scyllitol and a diborate recovery mixture; and
 c) recycling of the diborate recovery mixture to provide an additional amount of substantially pure scyllitol.

In some embodiments of the third aspect, said recycling of the diborate recovery mixture comprises the steps of:
 d) conversion of the diborate recovery mixture to recovered scyllitol diborate;
 e) isolation of the recovered scyllitol diborate from step d) as a solid;

f) conversion of the recovered scyllitol diborate to scyllitol, thereby forming a second scyllitol mixture;

g) isolation of the scyllitol as a solid from the second scyllitol mixture to provide the additional amount of substantially pure scyllitol and an additional diborate recovery mixture.

In some embodiments of the third aspect, the recycling steps are performed on the additional diborate recovery mixture, and optionally repeating the recycling steps 1, 2, 3, 4, 5, 6, 7, 8, 9, or 10 times on each subsequent diborate recovery mixture, thereby providing additional amounts of substantially pure scyllitol.

In some embodiments of the third aspect, step a) comprises a hydrolysis reaction. In some embodiments, the hydrolysis reaction is mediated by a catalyst, preferably wherein the catalyst is an acid, such as hydrochloric acid, sulfuric acid, nitric acid or phosphoric acid, preferably sulfuric acid or hydrochloric acid, preferably hydrochloric acid. In some embodiments, the hydrolysis reaction is performed in an aqueous acidic solution, preferably wherein the aqueous acidic solution is about 1N acid, preferably 1N HCl. In some embodiments, the hydrolysis reaction comprises combining scyllitol diborate with about 8-12 volumes of aqueous acid, preferably about 10 volumes of about 1N acid, preferably 1N HCl. In some embodiments, the hydrolysis reaction is performed at high temperature, such as at a temperature in the range of about 75-95° C., preferably about 85-95° C.

In some embodiments of the third aspect, step a) is monitored by measurement of pH. In some embodiments, step a) is complete when the reaction is at a pH of less than about 2.0.

In some embodiments of the third aspect, step a) comprises precipitation of scyllitol in the first scyllitol mixture. In one embodiment, the precipitation comprises cooling of the first scyllitol mixture, preferably cooling the first scyllitol mixture to a temperature in the range of about 20-30° C. In one embodiment, step a) further comprises agitation of the cooled scyllitol mixture at about 20-30° C. to provide a slurry.

In some embodiments of the third aspect, step b) comprises filtration.

In some embodiments of the third aspect, step d) comprises reaction of the diborate recovery mixture in a basic aqueous reaction mixture. In some embodiments, step d) comprises the addition of base to the diborate recovery mixture. In some embodiments, base is added until the reaction mixture is at a pH in the range of about 9-10. In some embodiments, the added base is NaOH.

In some embodiments of the third aspect, step d) is performed at high temperature, preferably at a temperature in the range of about 80-90° C.

In some embodiments of the third aspect, step d) further comprises precipitation of the recovered scyllitol diborate from the reaction mixture. In some embodiments, the precipitation comprises cooling the reaction mixture, preferably cooling to a temperature of about 20-30° C. In some embodiments, step d) further comprises agitation of the cooled reaction mixture at about 20-30° C. to provide a slurry.

In some embodiments of the third aspect, step e) comprises filtration.

In some embodiments of the third aspect, step f) comprises a hydrolysis reaction. In some embodiments, the hydrolysis reaction is mediated by a catalyst, preferably wherein the catalyst is an acid, such as hydrochloric acid, sulfuric acid, nitric acid or phosphoric acid, preferably sulfuric acid or hydrochloric acid, preferably hydrochloric acid. In some embodiments, the hydrolysis reaction is performed in an aqueous acidic solution, preferably in aqueous 1N acid, preferably 1N HCl. In some embodiments, the hydrolysis reaction comprises combining isolated recovered scyllitol diborate with about 8-12 volumes of aqueous acid, preferably about 10 volumes of about 1N acid, preferably 1N HCl. In some embodiments, the hydrolysis reaction is performed at high temperature, preferably at a temperature in the range of about 85-95° C.

In some embodiments of the third aspect, step f) further comprises precipitation of scyllitol in the second scyllitol mixture. In some embodiments, the precipitation comprises cooling of the second scyllitol mixture, preferably cooling to a temperature in the range of about 20-30° C. In some embodiments, step f) further comprises agitating the cooled solution at about 20-30° C. to provide a slurry.

In some embodiments of the third aspect, step g) comprises filtration.

In some embodiments of the third aspect, the scyllitol diborate used in step a) is obtained from any manufacturing process that comprises the steps of reacting scyllitol in a mixture to form scyllitol diborate, and isolating the scyllitol diborate from the mixture.

In a preferred embodiment of the third aspect, the method is a large scale process, for example, the process results in greater than about 1 kg, also about 2 kg, also about 5 kg, also about 10 kg, also about 50 kg, preferably greater than about 100 kg, also greater than about 200 kg, also about 500 kg, also about 1000 kg, also about 5000 kg, also about 8000 kg, also about 10000 kg, also about 14000 kg of substantially pure scyllitol. In some embodiments, the process results in about 1-14000 kg, also about 1-10000 kg, also about 1-8000 kg, also about 1-5000 kg, also about 10-14000 kg, also about 10-8000 kg, also about 50-14000 kg, also about 50-10000 kg, also about 50-8000 kg, also about 50-5000 kg, also about 50-3000 kg, also about 50-1000 kg, also about 50-500 kg, preferably about 50-200 kg of substantially pure scyllitol. In some embodiments, these amounts are obtained from one batch, i.e. step a) is performed once with scyllitol diborate. In some embodiments, one or more additional batches can be combined with a first batch to provide a commercial lot of substantially pure scyllitol.

In a fourth aspect, a method of preparing substantially pure scyllitol is provided comprising the steps of:

a) Subjecting a first mixture comprising myo-inositol to a process that converts at least a portion of the myo-inositol to scyllitol, thereby forming a second mixture;

b) converting the scyllitol in the second mixture to scyllitol diborate, thereby forming a third mixture;

c) isolating the scyllitol diborate as a solid from the third mixture to provide isolated scyllitol diborate and a first inositol recovery mixture;

d) converting the isolated scyllitol diborate to scyllitol, thereby forming a fourth mixture;

e) isolating the scyllitol as a solid from the fourth mixture to provide isolated substantially pure scyllitol and a first diborate recovery mixture;

f) combining the first inositol recovery mixture with additional myo-inositol to form a fifth mixture;

g) repeating steps a) through c) on the fifth mixture to provide additional isolated scyllitol diborate and a second inositol recovery mixture; and h) repeating step d) with the additional isolated scyllitol diborate, thereby forming a sixth mixture, and repeating step e) with the sixth mixture to provide additional isolated substantially pure scyllitol and a second diborate recovery mixture.

In some embodiments of the fourth aspect, in step e) and step h) the substantially pure scyllitol is isolated by crystallization followed by filtration. In some embodiments, the crystallized scyllitol is washed.

In some embodiments of the fourth aspect, the isolated substantially pure scyllitol from step e) and step h) are combined. In some embodiments, isolated substantially pure scyllitol from step e) and step h) is washed prior to or after combining, or washed both prior to and after combining.

In some embodiments of the fourth aspect, steps f) through h) are repeated using the second inositol recovery mixture from step g) in step f) to provide additional isolated substantially pure scyllitol, a third inositol recovery mixture and a third diborate recovery mixture.

In some embodiments of the fourth aspect, the steps f) through h) are repeated using any subsequent inositol recovery mixture (e.g. the third inositol recovery mixture, and further subsequent inositol recovery mixture generated for subsequent recycling) in step f) to provide additional isolated substantially pure scyllitol, additional inositol recovery mixture and additional diborate recovery mixture.

In some embodiments of the fourth aspect, the method further comprises the steps of: i) reacting the first diborate recovery mixture from step e) to form a recovered scyllitol diborate mixture; j) isolating the recovered scyllitol diborate from the recovered scyllitol diborate mixture; and k) repeating steps d) and e) with the recovered scyllitol diborate, thereby providing additional isolated substantially pure scyllitol and additional diborate recovery mixture.

In some embodiments of the fourth aspect, steps i) through k) are repeated using one or more other diborate recovery mixtures (e.g. second, third, and additional diborate recovery mixtures) to provide additional isolated substantially pure scyllitol. Any diborate recovery mixture can be taken through steps i) through k) individually, or any one or more diborate recovery mixtures can be combined and taken through steps i) through k).

In some embodiments of the fourth aspect, step a) comprises a stereoisomerization process. In some embodiments the stereoisomerization in step a) is mediated by a catalyst. In some embodiments, the catalyst is sponge nickel. In some embodiments, the catalyst is removed prior to step b). In some embodiments the catalyst is removed by filtration. In some embodiments, this filtration is performed at high temperature, such as at a temperature in the range of about 50-95° C., preferably in the range of about 70-95° C. In some embodiments the stereoisomerization in step a) is performed at high temperature, such as at a temperature of about 90-100° C. In some embodiments the stereoisomerization in step a) is performed in aqueous base. In one embodiment the stereoisomerization in step a) is performed at a pH in the range of about 8-12.

In some embodiments of the fourth aspect, step a) comprises an enzymatic process, or a bio-conversion process.

In some embodiments of the fourth aspect, step b) comprises reaction with sodium tetraborate. In some embodiments reaction with sodium tatraborate is performed at high temperature, such as at a temperature in the range of about 75-95° C., preferably at a temperature in the range of about 80-90° C. In some embodiments reaction with sodium tatraborate is performed at a pH in the range of about 8-11, preferably in the range of about 9-10. In some embodiments, step b) comprises adding base, preferably NaOH, to bring the mixture to a pH within the range of about 8-11, preferably about 9-10. In a preferred embodiment, reaction with sodium tatraborate is performed at a temperature in the range of about 80-90° C. and a pH in the range of about 9-10.

In some embodiments of the fourth aspect, step b) comprises reaction with boric acid. In some embodiments reaction with boric acid is performed at high temperature, such as at a temperature in the range of about 75-95° C., preferably at a temperature in the range of about 80-90° C. In some embodiments reaction with boric acid is performed at a pH in the range of about 8-11, preferably in the range of about 9-10. In some embodiments, step b) comprises adding base, preferably NaOH, to bring the mixture to a pH within the range of about 8-11, preferably about 9-10. In a preferred embodiment, reaction with boric acid is performed at a temperature in the range of about 80-90° C. and a pH in the range of about 9-10.

In some embodiments of the fourth aspect, step b) comprises precipitating scyllitol diborate. In some embodiments, step b) comprises cooling the mixture, preferably to a temperature in the range of 20-30° C. In some embodiments, step b) further comprises agitating the mixture at about 20-30° C. to provide a slurry.

In some embodiments of the fourth aspect, step c) comprises filtration.

In some embodiments of the fourth aspect, step d) comprises a hydrolysis reaction. In some embodiments, the hydrolysis reaction is mediated by a catalyst. In some embodiments the catalyst is an acid, such as hydrochloric acid, sulfuric acid, nitric acid or phosphoric acid, preferably sulfuric acid or hydrochloric acid, preferably hydrochloric acid. In some embodiments, the hydrolysis reaction is performed in an aqueous acidic solution, preferably wherein the aqueous acidic solution is about 1N acid, preferably 1N HCl. In some embodiments, the hydrolysis reaction comprises combining isolated scyllitol diborate with about 8-12 volumes of aqueous acid. In some embodiments, the hydrolysis reaction comprises combining isolated scyllitol diborate with about 10 volumes of about 1N acid, preferably 1N HCl. In some embodiments, the hydrolysis reaction is performed at high temperature, such as at a temperature in the range of about 75-95° C., preferably in the range of about 85-95° C.

In some embodiments of the fourth aspect, step d) is monitored by measurement of pH of the mixture. In some embodiments, step d) is complete when the reaction is at a pH of less than 2.0.

In some embodiments of the fourth aspect, step d) comprises precipitation of scyllitol in the fourth mixture. In some embodiments, the precipitation comprises cooling of the fourth mixture, such as cooling to a temperature in the range of about 20-30° C. In some embodiments, step d) further comprises agitation of the cooled mixture, preferably at 20-30° C. to provide a slurry.

In some embodiments of the fourth aspect, step e) comprises filtration.

In some embodiments of the fourth aspect, step i) comprises reaction of the first diborate recovery mixture in a basic aqueous reaction mixture. In some embodiments, the basic aqueous reaction mixture is reacted at high temperature, such as at a temperature in the range of about 80-90° C. In some embodiments, step i) comprises addition of base to the first diborate recovery mixture, preferably wherein base is added until the reaction mixture is at a pH in the range of about 9-10. In some embodiments, the added base is NaOH. In some embodiments, step i) further comprises precipitation of the recovered scyllitol diborate from the reaction mixture, preferably wherein precipitation comprises cooling the reaction mixture, preferably cooling to a temperature in the range of about 20-30° C. In some embodiments, step i) further comprises agitation of the reaction mixture at about 20-30° C. to provide a slurry.

In some embodiments of the fourth aspect, step j) comprises filtration.

In a preferred embodiment of the fourth aspect, the method is a large scale process, for example, the process results in greater than about 1 kg, also about 2 kg, also about 5 kg, also about 10 kg, also about 50 kg, preferably greater than about 100 kg, also greater than about 200 kg, also about 500 kg, also about 1000 kg, also about 5000 kg, also about 8000 kg, also about 10000 kg, also about 14000 kg of substantially pure scyllitol. In some embodiments, the process results in about 1-14000 kg, also about 1-10000 kg, also about 1-8000 kg, also about 1-5000 kg, also about 10-14000 kg, also about 10-8000 kg, also about 50-14000 kg, also about 50-10000 kg, also about 50-8000 kg, also about 50-5000 kg, also about 50-3000 kg, also about 50-1000 kg, also about 50-500 kg, preferably about 50-200 kg of substantially pure scyllitol. In some embodiments, these amounts are obtained from one batch, i.e. step a) is performed once with myo-inositol (i.e. initial use of myo-inositol in step a), inositol recovery mixture is further combined with additional myo-inositol and processed according to the method of step a) as part of a first batch, as described in step g) of the fourth aspect). In some embodiments, one or more additional batches can be combined with a first batch to provide a commercial lot of substantially pure scyllitol.

In a fifth aspect, method of preparing substantially pure scyllitol is provided comprising the steps of:
  a) Subjecting a first mixture comprising myo-inositol to a process that converts at least a portion of the myo-inositol to scyllitol, thereby forming a second mixture;
  b) converting the scyllitol in the second mixture to scyllitol diborate, thereby forming a third mixture;
  c) isolating the scyllitol diborate as a solid from the third mixture to provide isolated scyllitol diborate and a first inositol recovery mixture;
  d) converting the isolated scyllitol diborate to scyllitol, thereby forming a fourth mixture;
  e) isolating the scyllitol as a solid from the fourth mixture to provide isolated substantially pure scyllitol and a first diborate recovery mixture;
  f) reacting the first diborate recovery mixture to form recovered scyllitol diborate in a recovered scyllitol diborate mixture;
  g) isolating the recovered scyllitol diborate from the recovered scyllitol diborate mixture; and
  h) repeating steps d) and e) with the recovered scyllitol diborate, thereby providing additional substantially pure scyllitol and a second diborate recovery mixture.

In some embodiments of the fifth aspect, steps f) through h) are repeated using the second diborate recovery mixture in step f), thereby providing additional substantially pure scyllitol and additional diborate recovery mixture. The additional diborate recovery mixture can also be recycled through steps f) through h), thereby providing additional substantially pure scyllitol and additional diborate recovery mixture.

In some embodiments of the fifth aspect, the method further comprises the steps of:
  i) combining the first inositol recovery mixture with additional myo-inositol to form a fifth mixture;
  j) repeating steps a) through c) on the fifth mixture to provide additional isolated scyllitol diborate and a second inositol recovery mixture; and
  k) repeating step d) with the additional isolated scyllitol diborate, thereby forming a sixth mixture, and repeating step e) with the sixth mixture to provide additional isolated substantially pure scyllitol and an additional diborate recovery mixture.

In some embodiments of the fifth aspect, steps f) through h) are repeated using one or more other diborate recovery mixtures (e.g. second or additional diborate recovery mixtures) to provide additional isolated substantially pure scyllitol. Any diborate recovery mixture can be taken through steps f) through h) individually, or any one or more diborate recovery mixtures can be combined and taken through steps f) through h).

In some embodiments of the fifth aspect, in step e) and step h) the substantially pure scyllitol is isolated by crystallization followed by filtration. In some embodiments, the crystallized scyllitol is washed.

In some embodiments of the fifth aspect, the isolated substantially pure scyllitol from step e) and step h) are combined. In some embodiments, isolated substantially pure scyllitol from step e) and step h) are washed prior to or after combining, or washed both prior to and after combining.

In some embodiments of the fifth aspect, steps i) through k) are repeated using the second inositol recovery mixture from step j) in step i) to provide additional isolated substantially pure scyllitol, a third inositol recovery mixture and additional diborate recovery mixture.

In some embodiments of the fifth aspect, the steps i) through k) are repeated using any subsequent inositol recovery mixture (e.g. the third inositol recovery mixture, and further additional inositol recovery mixture(s) generated from subsequent recycling) in step f) to provide additional isolated substantially pure scyllitol, additional inositol recovery mixture and additional diborate recovery mixture.

In some embodiments of the fifth aspect, step a) comprises a stereoisomerization process. In some embodiments the stereoisomerization in step a) is mediated by a catalyst. In some embodiments, the catalyst is sponge nickel. In some embodiments, the catalyst is removed prior to step b). In some embodiments the catalyst is removed by filtration. In some embodiments, this filtration is performed at high temperature, such as at a temperature in the range of about 50-95° C., preferably in the range of about 70-95° C. In some embodiments the stereoisomerization in step a) is performed at high temperature, such as at a temperature of about 90-100° C. In some embodiments the stereoisomerization in step a) is performed in aqueous base. In one embodiment the stereoisomerization in step a) is performed at a pH in the range of about 8-12.

In some embodiments of the fifth aspect, step a) comprises an enzymatic process, or a bio-conversion process.

In some embodiments of the fifth aspect, step b) comprises reaction with sodium tetraborate. In some embodiments reaction with sodium tatraborate is performed at high temperature, such as at a temperature in the range of about 75-95° C., preferably at a temperature in the range of about 80-90° C. In some embodiments reaction with sodium tatraborate is performed at a pH in the range of about 8-11, preferably in the range of about 9-10. In some embodiments, step b) comprises adding base, preferably NaOH, to bring the mixture to a pH within the range of about 8-11, preferably about 9-10. In a preferred embodiment, reaction with sodium tatraborate is performed at a temperature in the range of about 80-90° C. and a pH in the range of about 9-10.

In some embodiments of the fifth aspect, step b) comprises reaction with boric acid. In some embodiments reaction with boric acid is performed at high temperature, such as at a temperature in the range of about 75-95° C., preferably at a temperature in the range of about 80-90° C. In some embodiments reaction with boric acid is performed at a pH in the range of about 8-11, preferably in the range of about 9-10. In some embodiments, step b) comprises adding base, preferably NaOH, to bring the mixture to a pH within the range of about 8-11, preferably about 9-10. In a preferred embodiment, reaction with boric acid is performed at a temperature in the range of about 80-90° C. and a pH in the range of about 9-10.

In some embodiments of the fifth aspect, step b) comprises precipitating scyllitol diborate. In some embodiments, step b) comprises cooling the mixture, preferably to a temperature in the range of 20-30° C. In some embodiments, step b) further comprises agitating the mixture at about 20-30° C. to provide a slurry.

In some embodiments of the fifth aspect, step c) comprises filtration.

In some embodiments of the fifth aspect, step d) comprises a hydrolysis reaction. In some embodiments, the hydrolysis reaction is mediated by a catalyst. In some embodiments the catalyst is an acid, such as hydrochloric acid, sulfuric acid, nitric acid or phosphoric acid, preferably sulfuric acid or hydrochloric acid, preferably hydrochloric acid. In some embodiments, the hydrolysis reaction is performed in an aqueous acidic solution, preferably wherein the aqueous acidic solution is about 1N acid, preferably 1N HCl. In some embodiments, the hydrolysis reaction comprises combining isolated scyllitol diborate with about 8-12 volumes of aqueous acid. In some embodiments, the hydrolysis reaction comprises combining isolated scyllitol diborate with about 10 volumes of about 1N acid, preferably 1N HCl. In some embodiments, the hydrolysis reaction is performed at high temperature, such as at a temperature in the range of about 75-95° C., preferably in the range of about 85-95° C.

In some embodiments of the fifth aspect, step d) is monitored by measurement of pH of the mixture. In some embodiments, step d) is complete when the reaction is at a pH of less than 2.0.

In some embodiments of the fifth aspect, step d) comprises precipitation of scyllitol in the fourth mixture. In some embodiments, the precipitation comprises cooling of the fourth mixture, such as cooling to a temperature in the range of about 20-30° C. In some embodiments, step d) further comprises agitation of the cooled mixture, preferably at 20-30° C. to provide a slurry.

In some embodiments of the fifth aspect, step e) comprises filtration.

In some embodiments of the fifth aspect, step f) comprises reaction of the first diborate recovery mixture in a basic aqueous reaction mixture. In some embodiments, the basic aqueous reaction mixture is reacted at high temperature, such as at a temperature in the range of about 80-90° C. In some embodiments, step f) comprises addition of base to the first diborate recovery mixture, preferably wherein base is added until the reaction mixture is at a pH in the range of about 9-10. In some embodiments, the added base is NaOH. In some embodiments, step f) further comprises precipitation of the recovered scyllitol diborate from the reaction mixture, preferably wherein precipitation comprises cooling the reaction mixture, preferably cooling to a temperature in the range of about 20-30° C. In some embodiments, step f) further comprises agitation of the reaction mixture at about 20-30° C. to provide a slurry.

In some embodiments of the fifth aspect, step g) comprises filtration.

In a preferred embodiment of the fifth aspect, the method is a large scale process, for example, the process results in greater than about 1 kg, also about 2 kg, also about 5 kg, also about 10 kg, also about 50 kg, preferably greater than about 100 kg, also greater than about 200 kg, also about 500 kg, also about 1000 kg, also about 5000 kg, also about 8000 kg, also about 10000 kg, also about 14000 kg of substantially pure scyllitol. In some embodiments, the process results in about 1-14000 kg, also about 1-10000 kg, also about 1-8000 kg, also about 1-5000 kg, also about 10-14000 kg, also about 10-8000 kg, also about 50-14000 kg, also about 50-10000 kg, also about 50-8000 kg, also about 50-5000 kg, also about 50-3000 kg, also about 50-1000 kg, also about 50-500 kg, preferably about 50-200 kg of substantially pure scyllitol. In some embodiments, these amounts are obtained from one batch, i.e. step a) is performed once with myo-inositol (i.e. initial use of myo-inositol in step a), inositol recovery mixture may be optionally further combined with additional myo-inositol and processed according to the method of step a) as part of a first batch, as described in the fifth aspect). In some embodiments, one or more additional batches can be combined with a first batch to provide a commercial lot of substantially pure scyllitol.

In a sixth aspect, the method of preparing substantially pure scyllitol from isolated scyllitol diborate and recycling the diborate recovery mixture to make more scyllitol diborate, and subsequently to make more substantially pure scyllitol, can be applied to any process comprising the step of forming scyllitol from isolated scyllitol diborate. Thus, a method of preparing substantially pure scyllitol is provided, comprising the steps of:
  a) converting scyllitol diborate to scyllitol, thereby forming a first scyllitol mixture;
  b) isolating the scyllitol as a solid from the first scyllitol mixture to provide a first amount of substantially pure scyllitol and a first diborate recovery mixture;
  c) reacting the first diborate recovery mixture to form recovered scyllitol diborate in a recovered scyllitol diborate mixture;
  d) isolating the recovered scyllitol diborate as a solid from the recovered scyllitol diborate mixture;
  e) repeating steps a) through d) using the recovered scyllitol diborate in step a), thereby providing additional substantially pure scyllitol and additional recovered scyllitol diborate; and
  f) optionally repeating steps a) through d) using the additional recovered scyllitol diborate in step a), thereby providing additional substantially pure scyllitol and additional recovered scyllitol diborate.

In some embodiments of the sixth aspect, the steps a) through d) are repeated successively using any additional recovered scyllitol diborate in step a).

In some embodiments of the sixth aspect, the scyllitol diborate used in step a) is isolated from any of the first, second or third aspects as described above.

In some embodiments of the sixth aspect, step a) comprises a hydrolysis reaction. In some embodiments, the hydrolysis reaction is mediated by a catalyst. In some embodiments the catalyst is an acid, such as hydrochloric acid, sulfuric acid, nitric acid or phosphoric acid, preferably sulfuric acid or hydrochloric acid, preferably hydrochloric acid. In some embodiments, the hydrolysis reaction is performed in an aqueous acidic solution, preferably wherein the aqueous acidic solution is about 1N acid, preferably 1N HCl. In some embodiments, the hydrolysis reaction comprises combining isolated scyllitol diborate with about 8-12 volumes of aqueous acid. In some embodiments, the hydrolysis reaction comprises combining isolated scyllitol diborate with about 10 volumes of about 1N acid, preferably 1N HCl. In some embodiments, the hydrolysis reaction is performed at high temperature, such as at a temperature in the range of about 75-95° C., preferably in the range of about 85-95° C.

In some embodiments of the sixth aspect, step a) is monitored by measurement of pH of the mixture. In some embodiments, step a) is complete when the reaction is at a pH of less than 2.0.

In some embodiments of the sixth aspect, step a) comprises precipitation of scyllitol in the first scyllitol mixture. In some embodiments, the precipitation comprises cooling of the first scyllitol mixture, such as cooling to a temperature in the range of about 20-30° C. In some embodiments, step d) further comprises agitation of the cooled mixture, preferably at 20-30° C. to provide a slurry.

In some embodiments of the sixth aspect, step b) comprises filtration.

In some embodiments of the sixth aspect, step c) comprises reaction of the first diborate recovery mixture in a basic aqueous reaction mixture. In some embodiments, the basic aqueous reaction mixture is reacted at high temperature, such as at a temperature in the range of about 80-90° C. In some embodiments, step c) comprises addition of base to the first diborate recovery mixture, preferably wherein base is added until the reaction mixture is at a pH in the range of about 9-10. In some embodiments, the added base is NaOH. In some embodiments, step c) further comprises precipitation of the recovered scyllitol diborate from the reaction mixture, preferably wherein precipitation comprises cooling the reaction mixture, preferably cooling to a temperature in the range of about 20-30° C. In some embodiments, step c) further comprises agitation of the reaction mixture at about 20-30° C. to provide a slurry.

In some embodiments of the sixth aspect, step d) comprises filtration.

In some embodiment of the sixth aspect, an isolated batch of scyllitol diborate is obtained for use in step a). The isolated batch may be in solution, part of a mixture or in solid form, and can be isolated from any process involving the conversion of scyllitol diborate to substantially pure scyllitol. For example, the process from which the scyllitol diborate is isolated may be as described herein, wherein the scyllitol diborate is isolated in solid form, such as by filtration of a precipitate. The scyllitol diborate can be converted to scyllitol by methods known in the art, or as described herein. In one embodiment, the conversion of isolated scyllitol diborate to scyllitol comprises a hydrolysis reaction. In one embodiment, the hydrolysis reaction is mediated by a catalyst. In one embodiment, the catalyst is an acid. In one embodiment, the acid is hycrochloric acid. In one embodiment, the isolated scyllitol diborate is obtained as a solid, and conversion of the isolated scyllitol diborate to scyllitol comprises the steps of: i) combining the isolated scyllitol diborate with aqueous acid to form a mixture; ii) heating the mixture to about 85-95° C.; iii) cooling the mixture; and iv) agitating the cooled mixture to form a slurry. In some embodiments, the isolation of scyllitol further comprises the steps of v) filtering the slurry from step iii) to isolate substantially purified scyllitol as a solid; and vi) optionally rinsing the filter cake with water; and vii) optionally drying the filter cake. In this case, the filtrate from filtering the slurry is the diborate recovery mixture. In some embodiments, the mixture of step i) is formed by adding hydrochloric acid until the pH of the mixture is less than 6.0, less than 5.0, less than 4.0, less than 3.0, or less than 2.0. In some embodiments, hydrochloric acid is added until the pH is in the range of 0.5 to 5.8. In some embodiments, isolated scyllitol diborate is combined with about 1N aqueous acid, preferably wherein the acid is HCl. In some embodiments, the conversion is monitored by measurement of pH, where the conversion is considered complete if the pH of the solution is less than 5.0, less than 4.0, less than 3.0, or preferably less than 2.0. In some embodiments, the mixture is cooled to about 20-30° C. for 2-4 hours. In some embodiment this mixture is agitated at about 20-30° C. for 2-4 hours.

In a preferred embodiment of the sixth aspect, the method is a large scale process, for example, the process results in greater than about 1 kg, also about 2 kg, also about 5 kg, also about 10 kg, also about 50 kg, preferably greater than about 100 kg, also greater than about 200 kg, also about 500 kg, also about 1000 kg, also about 5000 kg, also about 8000 kg, also about 10000 kg, also about 14000 kg of substantially pure scyllitol. In some embodiments, the process results in about 1-14000 kg, also about 1-10000 kg, also about 1-8000 kg, also about 1-5000 kg, also about 10-14000 kg, also about 10-8000 kg, also about 50-14000 kg, also about 50-10000 kg, also about 50-8000 kg, also about 50-5000 kg, also about 50-3000 kg, also about 50-1000 kg, also about 50-500 kg, preferably about 50-200 kg of substantially pure scyllitol. In some embodiments, these amounts are obtained from one batch, i.e. step a) is performed once with scyllitol diborate (i.e. scyllitol diborate as starting material, the method of step a) is repeated on recovered scyllitol diborate as part of a first batch as described in step e) of the sixth aspect). In some embodiments, one or more additional batches can be combined with a first batch to provide a commercial lot of substantially pure scyllitol.

In a seventh aspect, a method of preparing substantially pure scyllitol is provided, comprising the steps of:
 a) Heating a mixture of scyllitol diborate in aqueous acid in a reaction vessel;
 b) Agitating the mixture at high temperature to obtain a solution;
 c) Cooling the solution to provide a second mixture comprising precipitated scyllitol;
 d) Agitating the cooled second mixture to provide a slurry comprising precipitated scyllitol;
 e) Filtering the slurry to isolate substantially pure scyllitol solid from a diborate recovery filtrate;
 f) Optionally rinsing the reaction vessel with about 1 volume of water and filtering the rinse through the substantially pure scyllitol solid;
 g) Optionally repeating step f);
 h) Heating the diborate recovery filtrate from step e), optionally combined with the rinse(s) from steps f) and g), in a second reaction vessel;
 i) Adding base to the diborate recovery filtrate, thereby forming a second mixture;
 j) Agitating the second mixture at high temperature;
 k) Cooling the second mixture;
 l) Agitating the second mixture to provide a second slurry;
 m) Filtering the second slurry to isolate recovered scyllitol diborate solid from a second filtrate;
 n) Optionally rinsing the reaction vessel with about 1 volume of water and filtering the rinse through the recovered scyllitol diborate solid;
 o) Optionally repeating step n);
 p) Recycling the recovered scyllitol diborate solid through steps a) through f) to provide additional substantially pure scyllitol solid and additional diborate recovery filtrate; and
 q) Combining the substantially pure scyllitol solids from steps e) and n) to provide a first amount of substantially pure scyllitol.

In some embodiments of the seventh aspect, step a) comprises about 10 volumes of about 1N acid, preferably 1N HCl. In some embodiments, the mixture is heated to about 85-95° C., preferably over about 2-3 hours.

In some embodiments of the seventh aspect, step b) comprises agitating the mixture at about 85-95° C., preferably for at least 10 minutes.

In some embodiments of the seventh aspect, step c) comprises cooling to about 20-30° C., preferably over about 3-4 hours.

In some embodiments of the seventh aspect, step d) comprises agitating at about 20-30° C.

In some embodiments of the seventh aspect, step h) comprises heating to about 80-90° C., preferably over about 2-3 hours.

In some embodiments of the seventh aspect, step i) comprises adding NaOH, preferably adding NaOH to bring the pH to within a range of about 9-10.

In some embodiments of the seventh aspect, step j) comprises agitating the second mixture at about 80-90° C., preferably for at least 1 hour.

In some embodiments of the seventh aspect, step k) comprises cooling the second mixture to about 20-30° C., preferably over about 3-4 hours.

In some embodiments of the seventh aspect, step l) comprises agitating the cooled second mixture at about 20-30° C., preferably for at least 1 hour.

In some embodiments of the seventh aspect, the method further comprises optionally recycling the additional diborate recovery filtrate from step p), optionally combined with rinses per steps f) and g), by following the methods of steps h) through m) to isolate additional recovered scyllitol diborate, and optionally recycling the additional scyllitol diborate through steps a) through f) to provide additional substantially pure scyllitol.

In some embodiments of the seventh aspect, the recycling of scyllitol diborate recovery filtrate to form additional recovered scyllitol diborate, and recycling the additional recovered scyllitol diborate, is repeated 1, 2, 3, 4, 5, 6, 7, 8, 9, or 10 times.

In a preferred embodiment of the seventh aspect, the method is a large scale process, for example, the process results in greater than about 1 kg, also about 2 kg, also about 5 kg, also about 10 kg, also about 50 kg, preferably greater than about 100 kg, also greater than about 200 kg, also about 500 kg, also about 1000 kg, also about 5000 kg, also about 8000 kg, also about 10000 kg, also about 14000 kg of substantially pure scyllitol. In some embodiments, the process results in about 1-14000 kg, also about 1-10000 kg, also about 1-8000 kg, also about 1-5000 kg, also about 10-14000 kg, also about 10-8000 kg, also about 50-14000 kg, also about 50-10000 kg, also about 50-8000 kg, also about 50-5000 kg, also about 50-3000 kg, also about 50-1000 kg, also about 50-500 kg, preferably about 50-200 kg of substantially pure scyllitol. In some embodiments, these amounts are obtained from one batch, i.e. step a) is performed once with scyllitol diborate (i.e. scyllitol diborate as starting material, the method of step a) is repeated on recovered scyllitol diborate as part of a first batch as described in the seventh aspect). In some embodiments, one or more additional batches can be combined with a first batch to provide a commercial lot of substantially pure scyllitol.

In an eighth aspect, a method of preparing substantially pure scyllitol is provided, comprising the steps of:
a) Combining inositol, sponge nickel and about 6 volumes of water (w/w inositol) in a reaction vessel, thereby providing a mixture;
b) Heating the mixture to about 95-100° C.;
c) Cooling the mixture to about 85-95° C. and filtering the mixture to remove the sponge nickel from filtrate;
d) Rinsing the reaction vessel with about 2 volumes of water at about 50-60° C.;
e) Filtering the rinse through the filtered nickel at about 50-60° C.;
f) Combining the filtrate from step c) and the rinse from step e) to provide a second mixture;
g) Combining the second mixture with $Na_2B_4O_7$ in a second reaction vessel to provide a third mixture;
h) Heating the third mixture to about 80-90° C.;
i) Adding NaOH to the third mixture to bring the pH to within a range of about 9-10;
j) Stirring the third mixture at 80-90° C.;
k) Cooling the third mixture to 20-30° C. over about 4-16 hours;
l) Agitating the third mixture at about 20-30° C. to provide a slurry;
m) Filtering the slurry to isolate scyllitol diborate solid from inositol recovery filtrate;
n) Optionally rinsing the reaction vessel with about 1 volume of water and filtering the rinse through the solid scyllitol diborate;
o) Optionally repeating step n);
p) Treating the isolated scyllitol diborate according to the methods of the seventh aspect (see paragraph [0137]) to provide substantially pure scyllitol;
q) Combining the inositol recovery filtrate from step m), optionally combined with the rinse(s) from steps n) and o), with additional inositol and additional sponge nickel in a third reaction vessel, thereby providing a fourth mixture;
r) Repeating steps b) through o) to provide additional isolated scyllitol diborate and additional inositol recovery filtrate;
s) Treating the additional isolated scyllitol diborate according to the methods of the seventh aspect to provide additional substantially pure scyllitol;
t) Combining the substantially pure scyllitol solids from steps p) and s) to provide a second amount of substantially pure scyllitol; and
u) Optionally combining the first amount of substantially pure scyllitol from the methods of the seventh aspect with the second amount of substantially pure scyllitol form step t).

In some embodiments of the eighth aspect, the additional inositol recovery filtrate from step r) is recycled according to steps q) through s) to provide additional substantially pure scyllitol.

In a preferred embodiment of the eighth aspect, the method is a large scale process, for example, the process results in greater than about 1 kg, also about 2 kg, also about 5 kg, also about 10 kg, also about 50 kg, preferably greater than about 100 kg, also greater than about 200 kg, also about 500 kg, also about 1000 kg, also about 5000 kg, also about 8000 kg, also about 10000 kg, also about 14000 kg of substantially pure scyllitol. In some embodiments, the process results in about 1-14000 kg, also about 1-10000 kg, also about 1-8000 kg, also about 1-5000 kg, also about 10-14000 kg, also about 10-8000 kg, also about 50-14000 kg, also about 50-10000 kg, also about 50-8000 kg, also about 50-5000 kg, also about 50-3000 kg, also about 50-1000 kg, also about 50-500 kg, preferably about 50-200 kg of substantially pure scyllitol. In some embodiments, these amounts are obtained from one batch, i.e. step a) is performed once and carried through the methods of the eighth aspect (optionally including combination with the first amount of scyllitol from the seventh aspect).

In some embodiments, one or more additional batches can be combined with a first batch to provide a commercial lot of substantially pure scyllitol.

In a ninth aspect, a method of preparing substantially pure scyllitol is provided, comprising the steps of:
a) obtaining an isolated batch of scyllitol diborate from any process comprising the formation of scyllitol from scyllitol diborate; and
b) treating the isolated batch of scyllitol diborate according to the methods of the third aspect (see paragraph [0069]), the sixth aspect (see paragraph [0126]), or the seventh aspect (see paragraph [0137]), to provide substantially pure scyllitol.

DETAILED DESCRIPTION OF THE INVENTION

Figure 1:
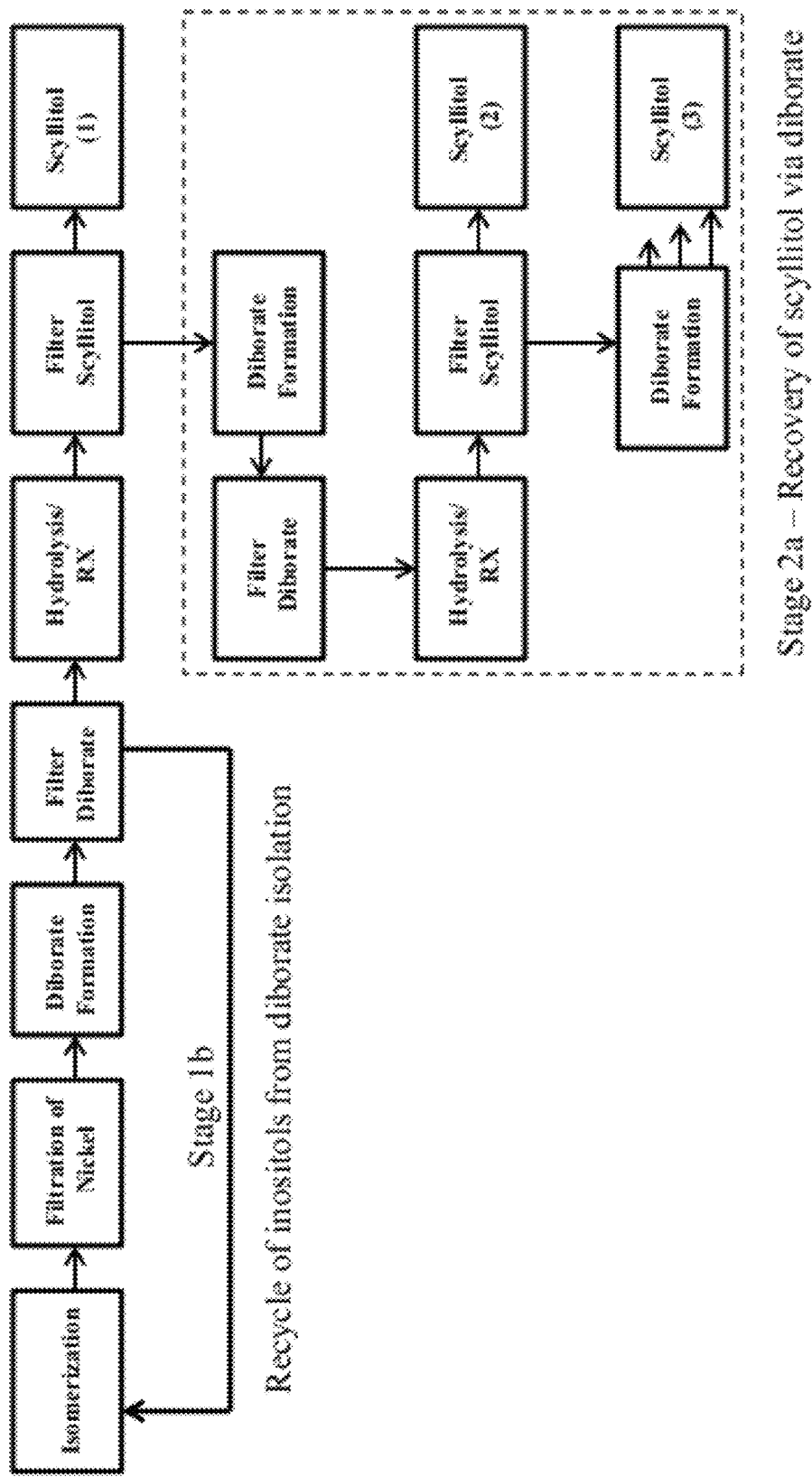
FIG. 1. Process-flow diagram of a pseudo-continuous route to scyllitol, starting from a solution containing any inositol stereoisomer or mixture of inositol stereoisomers.

Methods of chemical synthesis for scyllitol and related compounds, including scyllitol diborate are provided. In a general aspect, methods comprise the steps of i) forming some amount of scyllitol from a solution of inositol, preferably myo-inositol, ii) conversion of the scyllitol to scyllitol diborate, iii) isolation of the scyllitol diborate, iv) conversion of the scyllitol diborate to scyllitol, and v) isolation of substantially pure scyllitol. In one aspect, the mixture remaining after isolation of the scyllitol diborate, i.e. an inositol recovery mixture, may be recycled to step i), optionally with addition of inositol, to form additional scyllitol, which can then be processed to the scyllitol diborate and substantially pure scyllitol. In one aspect, the mixture from the isolation of the substantially purified scyllitol, referred to herein as the diborate recovery mixture, may also be recycled, for example the diborate recovery mixture may be reacted to form recovered scyllitol diborate, which can be isolated and recycled to step iv) and through the appropriate steps to form additional substantially pure scyllitol. These recycling steps provide improved efficiency and overall yield of the substantially pure scyllitol. In one aspect, the method comprises starting from an isolated scyllitol diborate, where the scyllitol diborate can be isolated from any process used to convert inositol, or other suitable starting material, to impure scyllitol which is purified through formation of the scyllitol diborate. In one aspect, the methods comprise the steps of non-specific stereoisomerization of a solution of inositol, conversion of scyllitol in the solution to scyllitol diborate, and isolation of the scyllitol diborate from the solution, followed by conversion of the scyllitol diborate to scyllitol, and isolation of substantially pure scyllitol.

The methods provided herein can be described generally by the following reaction scheme.

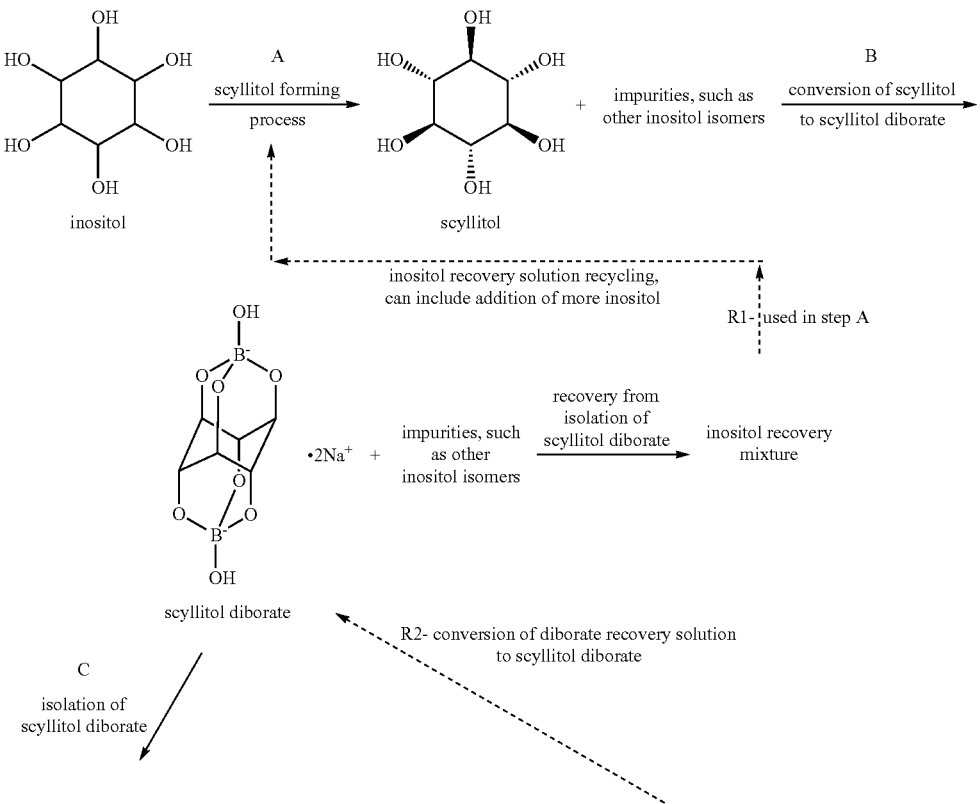

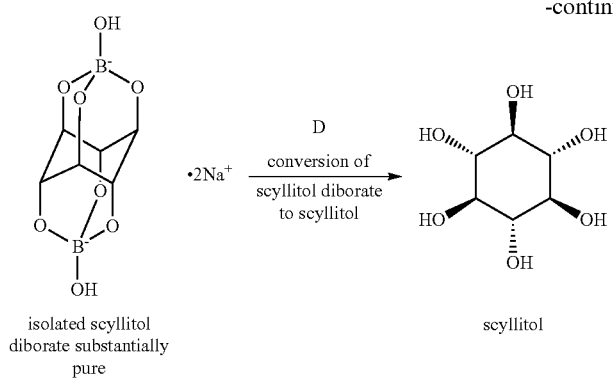

isolated scyllitol diborate substantially pure

D
conversion of scyllitol diborate to scyllitol scyllitol diborate recovery mixture
recovery from isolation of substantially pure scyllitol E
Isolation of substantially pure scyllitol

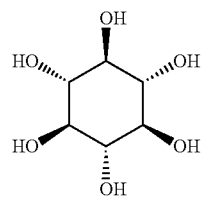

substantiall pure scyllitol

Step A involves conversion of a mixture comprising inositol, preferably myo-inositol, to a mixture comprising scyllitol, by methods known in the art, or as described herein. Step A could involve additional steps where inositol is converted to an intermediate, and the intermediate converted to scyllitol. In a preferred method, step A involves stereoisomerization of inositol (preferably myo-inositol) where the stereoisomerization results in some amount of scyllitol, along with other inositol isomers. In a preferred embodiment, stereoisomerization includes a catalyst (e.g. sponge nickel) and is performed at high temperature (e.g. 95-100° C.) in an aqueous mixture. In some embodiments, the catalyst is removed, for example by filtration through Celite® at high temperature, optionally rinsing the reaction vessel and filtering through the Celite.

Step B involves the conversion of the scyllitol formed in step A into scyllitol diborate by methods known in the art, or as described herein. In some instances, the reaction mixture from Step A is reacted with boric acid at high pH (e.g. pH 8-12, also 8-11, preferably 9-10) and elevated temperature (e.g. 80-90° C.). In a preferred embodiment, the reaction mixture from step A is reacted with $Na_2B_4O_7$ at high pH (e.g. pH 8-12, also 8-11, preferably 9-10) and elevated temperature (e.g. 80-90° C.). Due to its relative insolubility, the scyllitol diborate can be isolated in substantially pure form by precipitation or crystallization, for example by cooling the mixture to about 20-30° C. The cooled mixture can be agitated to form a slurry. Isolation of the scyllitol diborate by step C results in substantially pure isolated scyllitol diborate solid and what is referred to herein as inositol recovery mixture (or solution, filtrate, supernatant). The scyllitol diborate is preferably isolated by filtration.

Step D involves the conversion of the substantially pure scyllitol diborate to scyllitol by methods known in the art or as described herein. In a preferred embodiment, the scyllitol diborate is converted to scyllitol by hydrolysis, for example by reacting an aqueous mixture at low pH (e.g. pH 1-5, preferably 1N acid, preferably hydrochloric acid) with heating (e.g. 70-95° C., preferably 85-95° C.). Isolation of the scyllitol by step E results in substantially pure scyllitol solid and what is referred to herein as diborate recovery mixture (or solution, filtrate, supernatant). The scyllitol is preferably precipitated by cooling the mixture and agitating to form a slurry, and isolated by filtration.

The overall process optionally includes recycling of the inositol recovery mixture and/or the diborate recovery mixture. In a preferred embodiment, the overall process includes one or both of recycling of the inositol recovery mixture and the diborate recovery mixture. The inositol recovery mixture can be used in step A, where in preferred embodiments, additional inositol is added prior to performing step A. It is understood that recycling of the inositol recovery mixture itself results in another batch of inositol recovery mixture, which can be similarly recycled. The product of step A for any recycled inositol recovery mixture is carried through to step E. Similarly, The diborate recovery mixture can be recycled by first converting the diborate recovery mixture to scyllitol diborate. In a preferred embodiment, the diborate recovery mixture is heated (e.g. 80-90° C.) at high pH (e.g. pH 9-10) and the resulting scyllitol diborate is precipitated from solution, e.g. by cooling to about 20-30° C. and agitating the cooled mixture to form a slurry. The scyllitol diborate can be isolated from the resulting slurry similarly to step C and carried through to step E to provide additional substantially pure scyllitol and additional diborate recovery mixture, which itself can be similarly recycled. Substantially pure scyllitol can be produced even with repeated recycling of either the inositol recovery mixture or the diborate recovery mixture, resulting in improved overall yields and cost saving from recycling these solutions. Purification of scyllitol from a mixture by converting the scyllitol to scyllitol diborate, isolating the substantially pure scyllitol diborate, and converting this to substantially pure scyllitol is used in many processes for the preparation of scyllitol. As such, recycling of the diborate recovery mixture as described herein, e.g. the process involving step D, step E, and the recycling process R2, followed by step C, step D, and Step E, is a unique recycling method that can be applied to a variety of known processes for the production of scyllitol, to provide improved overall yields of scyllitol at reduced cost.

Figure 2:
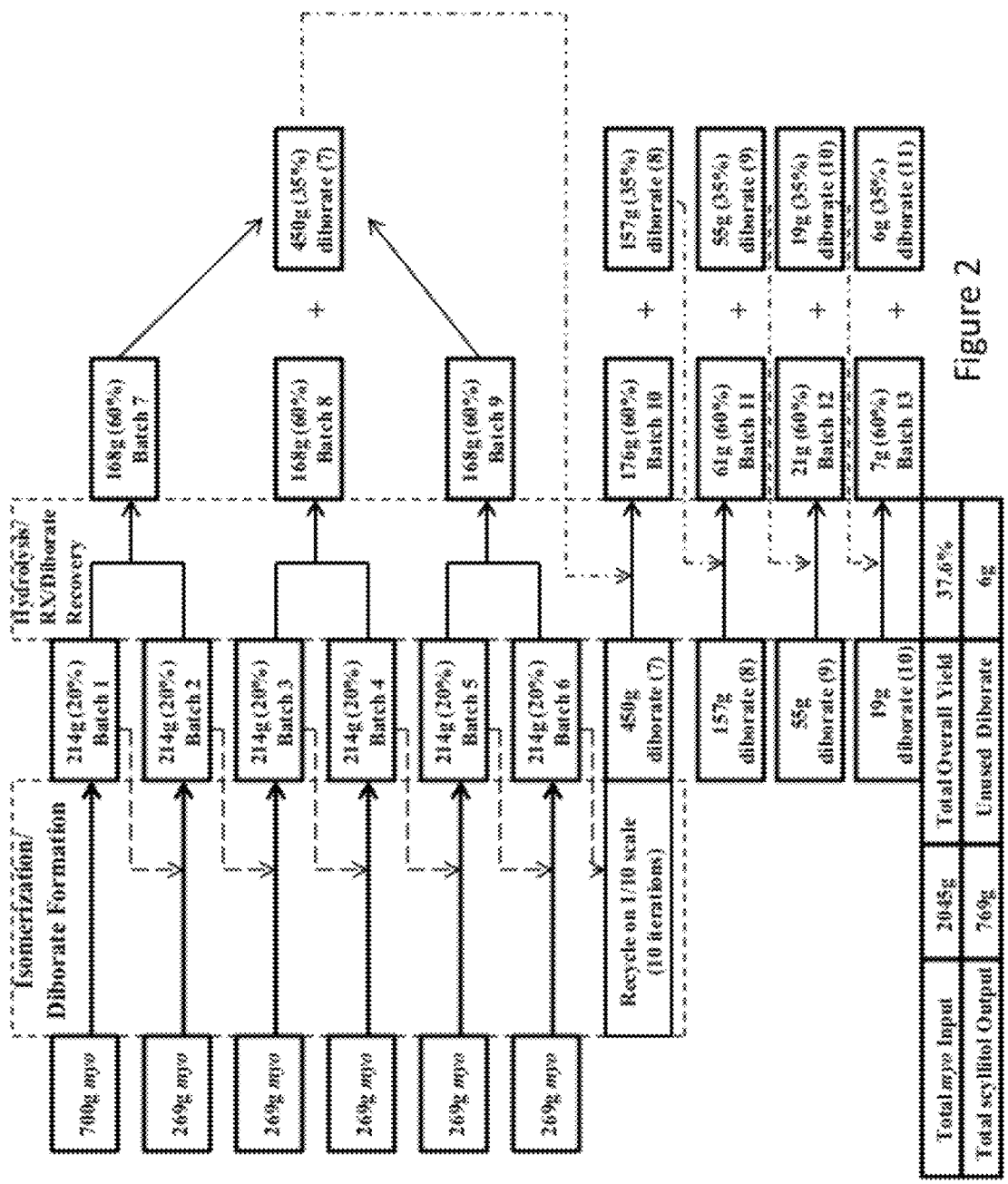
FIG. 2. Process for the synthesis of scyllitol from myo-inositol. The raw material charges and predicted yields (both step-wise and overall) are shown. The left gray panel represents the isomerization and scyllitol diborate formation reactions, and the right gray panel represents the hydrolysis and diborate recovery reactions.

The recycling method R1 can be performed repeatedly, at least 1-5 time, also 1-10 times, also 1-15 times or more to provide suitably pure scyllitol diborate. It is understood that with each repeat of R1 through steps A through C to form additional scyllitol diborate, the resulting scyllitol diborate can be carried through to the conversion to scyllitol (step D) individually, or the isolated scyllitol diborate resulting from repeated recyclings may be combined prior to conversion to scyllitol. As shown in FIG. 2 and in the Examples, the scyllitol diborate from this recycling step resulted in substantially pure scyllitol even after repeating this recycling step 15 times. Similarly, the recycling method R2 can be performed repeatedly, at least 1-5 times, also 1-10 times, also 1-15 times or more to provide suitably pure scyllitol. It is understood that each recycling step R1 results in a diborate recovery mixture, where the diborate recovery mixture may be recycled using method R2 individually, or various diborate recovery mixtures may be combined prior to performing recycling method R2. Similarly, when diborate recovery mixture is individually recycled, the resulting isolated scyllitol diborate from individual recoveries can be combined prior to conversion to scyllitol by step D, or can be individually converted to scyllitol by step D. It is understood that the overall process, with optional recycling steps, may result in isolation of substantially pure scyllitol from the initial formation of scyllitol diborate, from scyllitol diborate that is the result of recycling step R1, and from scyllitol diborate that is the result of recycling step R2, and any iterations thereof, where each formation of isolated scyllitol can be combined to provide a final batch of substantially pure scyllitol. A first batch process (i.e. a single production run) is considered any process where the initial step A is performed on an initial starting material, such as inositol, and carried through the process with or without recycling steps R1 and R2 (e.g. recycling as a continuous or pseudo-continuous part of the overall process), and all resulting substantially pure scyllitol is combined to form a first batch of scyllitol. Suitably pure scyllitol from additional batches, or additional production runs, may optionally be combined with a first batch to provide a larger quantity of substantially pure scyllitol. Typically, production of a single batch of scyllitol from the methods as described herein provides about 1-8000 kg, also about 1-5000 kg, also about 10-8000 kg, also about 10-5000 kg, also about 50-8000 kg, also about 50-5000 kg, also about 50-1000 kg, also about 50-500 kg, also about 50-200 kg, or about 50-100 kg scyllitol. When recycling steps are included in the process, the amount of scyllitol produced can be increased, for example, about 1-14000 kg, also about 1-10000 kg, also about 1-8000 kg, also about 10-14000 kg, also about 10-10000 kg, also about 10-8000 kg, also about 50-14000 kg, also about 50-10000 kg, also about 50-8000 kg, also about 50-5000 kg, also about 50-2000 kg, also about 50-1000 kg, also about 50-500 kg, also about 50-400 kg, also about 50-300 kg, or about 50-200 kg of substantially pure scyllitol can be produced in one batch of processing with recycling.

The methods described herein are particularly suited to large scale processes, meaning that the methods are performed at an industrial scale or commercial scale, such that large quantities of substantially pure scyllitol are prepared for commercial use, such as for human use, e.g. as a pharmaceutical, or as a food supplement. Any of the methods as described herein may be used in an industrial or commercial scale process to produce greater than about 1 kg, also about 2 kg, also about 5 kg, also about 10 kg, also about 50 kg, preferably greater than about 100 kg, also greater than about 500 kg, also about 1000 kg, also about 5000 kg, also about 8000 kg, also about 10000 kg, also greater than about 14000 kg of substantially pure scyllitol, preferably where such quantities are prepared in one batch, i.e. one lot of starting material is taken through the methods as described herein, with or without recycling. Similarly, where methods are provided for the production of scyllitol diborate, which can subsequently be converted to substantially pure scyllitol, the methods may be used in an industrial or commercial scale process to produce greater than about 1 kg, also about 2 kg, also about 5 kg, also about 10 kg, also about 50 kg, also about 100 kg, also about 200 kg, also about 300 kg, also about 500 kg, also about 1000 kg, also about 2000 kg, also about 3000 kg, also about 4000 kg, also about 5000 kg, also about 8000 kg, also about 10000 kg, also greater than about 12000 kg for example about 1-12000 kg, also about 10-12000 kg, also about 50-12000 kg, also about 50-10000 kg, also about 50-8000 kg, also about 50-5000 kg, also about 50-000 kg, also about 50-3000 kg, also about 50-2000 kg, also about 50-1000 kg, also about 50-500 kg, also about 50-300 kg of substantially pure scyllitol diborate, where such quantities are prepared in one batch, i.e. one lot of starting material is taken through the methods as described herein, with or without recycling, or may be the result of combination of two or more batches, i.e. a first lot of starting material provides one batch, a second lot of starting material a second batch, and so forth, and the two or more batches are combined for further processing to scyllitol; and production of more than about 500 kg, about 1000 kg, about 2000 kg, about 3000 kg, about 4000 kg, also about 5000 kg, also about 8000 kg, also about 10000 kg, also about 14000 kg of scyllitol. Thus, the methods as described herein are suitable for the commercial production of about 1-14000 kg, also about 1-10000 kg, also about 1-8000 kg, also about 1-5000 kg, also about 10-14000 kg, also about 10-8000 kg, also about 10-5000 kg, also about 50-14000 kg, also about 50-10000 kg, also about 50-8000 kg, also about 50-5000 kg, also about 50-4000 kg, also about 50-3000 kg, also about 50-2000 kg, also about 50-1000 kg, also about 50-500 kg, also about 50-300 kg, also about 50-200 kg of scyllitol. It is understood that methods as described herein can be used to produce such large scale quantities of scyllitol or scyllitol diborate even without the recycling steps (i.e. either recycling of the inositol recovery mixture (in the production of scyllitol diborate or scyllitol), or recycling of the diborate recovery mixture (in the production of scyllitol), or recycling of both the inositol recovery mixture and the diborate recovery mixture (in the production of scyllitol)), and that the recycling steps provide an even more cost effective and efficient process for the large scale production of substantially pure diborate and/or substantially pure scyllitol. It is also understood that methods as described herein can be used with one batch of starting material to produce one batch of substantially pure scyllitol or substantially pure scyllitol diborate. For example, the method of step a) in some of the various aspects described herein is performed once on a starting material (although in some aspects, the method of step a) may be repeated as a recycling step, this would be part of a first batch) to provide a first batch of product. In some instance, this batch is designated as a lot of the desired product. In some instances, additional batches (i.e. repeating the process on a new batch of starting material, e.g. step a)) can be combined to form a single lot of material.

The inositol used in the methods as described herein may be from any source and may contain any ratio of stereoisomers. In preferred embodiments, however, the inositol used according to the methods as described herein is myo-inositol.

As would be understood by one of ordinary skill in the art, the terms scyllitol and scyllo-inositol are synonymous and are used interchangeably throughout the instant application. The term "substantially pure" as it applies to scyllitol means that scyllitol is produced of suitable purity and low levels of impurities such as nickel, aluminum and boron, and would be suitable for use in animal studies and in human clinical trials, or for use in humans generally, for example as a pharmaceutical or as a food supplement. In one aspect, substantially pure scyllitol is 97-103% purity by HPLC (w/w), not more than 20 ppm heavy metal content, not more than 20 ppm nickel content, and not more than 50 ppm aluminum content. Scyllitol diborate, as used herein, is a salt complex of scyllitol diborate, for example dipotassium or disodium salt complex, preferably scyllitol diborate is the disodium salt complex. The term "substantially pure" as it applies to scyllitol diborate means that scyllitol diborate is produced of suitable purity to be used in the methods as described herein to produce substantially pure scyllitol.

As would be understood by one skilled in the art, ranges of reaction variables, such as concentrations, temperature, and pH, can vary slightly without significantly affecting the outcome of the reaction. For example, a temperature range of about 80-90° C. does not need to fall exactly within the range of 80 to 90, or an aqueous solution of 1N HCl can vary slightly form 1N and still result in an efficient reaction.

Reaction steps as described herein typically describe reaction mixtures generally, where such mixtures could be, for example, a solution or a slurry. Typically, when discussing recycling of isolated reaction components, the recycled component is described as a mixture, such as inositol recovery mixture or diborate recovery mixture. These mixtures are typically isolated from a solid product, e.g. by filtration or centrifugation, and could also be referred to as filtrates, supernatants or solutions.

The inositol used as a starting material in the methods as described herein may be from any suitable source, either natural or synthetic. The inositol may be a single stereoisomeric form or may be a mixture of stereoisomers. Without intending to be bound by theory, it is believed that the non-specific stereoisomerization reaction generates mixtures of stereoisomers that reflect the thermodynamic stability of the various stereoisomers. Regardless of the initial distribution of inositol stereoisomers in the solution used in the subject methods, some amount of scyllitol will be generated from the mixture by the non-specific stereoisomerization of the inositol solution. The conversion of the scyllitol generated by the non-specific stereoisomerization reaction into scyllitol diborate traps the desired stereoisomer and allows its efficient isolation from the mixture. Repetition of the non-specific stereoisomerization reaction on the solution that remains after the scyllitol is converted to scyllitol diborate allows even more efficient conversion of the inositol starting material into scyllitol. In some cases, additional inositol may be added to the solution to replenish what was lost in the first reaction, before repeating the stereoisomerization.

In some embodiments, the solution of inositol is an aqueous solution. The use of an aqueous solution of inositol in the methods as described herein provides environmental benefits over the traditional use of potentially toxic and expensive organic solvents. The methods as described herein may in some cases, however, be carried out in aqueous solutions that also contain one or more organic solvents. In some embodiments, the organic solvent comprises no more than 50% volume:volume of the total solution. In other embodiments, the organic solvent comprises no more than 40%, 30%, 20%, or even 10% volume:volume of the total solution. In preferred embodiments the organic solvent is ethanol, although other organic solvents may find utility in the chemical syntheses as described in the methods herein. In highly preferred embodiments, the solution is aqueous and contains no added organic solvent.

The non-specific stereoisomerization of inositol to scyllitol can be a relatively inefficient process, perhaps because the equilibrium level of scyllitol in a mixture of inositol stereoisomers is low. As described above, in one aspect, methods for the preparation of scyllitol provide increased efficiency of scyllitol synthesis by repetition of the non-specific stereoisomerization reaction on the mixture that remains after conversion of scyllitol to scyllitol diborate and isolation of the scyllitol diborate from the mixture. The remaining mixture from this process step may be referred to herein as inositol recovery mixture, inositol recovery supernatant, inositol recovery solution, or inositol recovery filtrate. In some embodiments, the steps of the method are therefore repeated on the inositol recovery mixture following isolation of the scyllitol diborate. The repeated steps to form additional scyllitol, then converting this to scyllitol diborate would result in a second inositol recovery mixture, which can also be similarly recycled. Thus repeat of the steps of the method on inositol recovery mixture is understood to mean that a first inositol recovery mixture is carried through the process steps to form additional scyllitol diborate and a second inositol recovery mixture. The second inositol recovery mixture is then carried through the steps of the method as the second repeat of the steps of the method to form scyllitol diborate, and so forth. In preferred embodiments, the steps of the method are repeated at least 1, 2, 3, 4, 5, 6, 7, 8, 9, or 10 times. In some embodiments, the steps are repeated on the inositol recovery mixture 1-5 times, 1-6 times, 1-7 times, 1-8 times, 1-9 times, 1-10 times, 1-11 times, 1-12 times, 1-13 times, 1-14 times, 1-15 times, or more than 15 times. In some embodiments, the steps of the method are repeated more than 10 times.

In some embodiments, the inositol recovery mixture is combined with additional inositol prior to repeating the steps of the method. The additional inositol replenishes the inositol that was converted to scyllitol and removed from the mixture by conversion to scyllitol diborate. Addition of inositol may also increase the concentration of inositol in solutions that have been diluted during the synthetic process. For example, the reaction mixture may be combined with solutions used to rinse the solid products of the reaction, such as, for example, the scyllitol diborate or the solid catalysts used to accelerate the stereoisomerization reaction. The charging of solutions used in the methods as described herein with additional inositol may therefore substantially increase the overall yield of the recycled reactions by increasing the rate or efficiency of the processes. The inositol added to the inositol recovery mixture prior to repeating the steps of the method to form scyllitol and converting this to scyllitol diborate, and subsequently converting this to substantially purified scyllitol, may be from any source and may contain any distribution of inositol stereoisomers. Preferably, however, the added inositol is myo-inositol.

The non-specific stereoisomerization reaction may be achieved by any appropriate method, as would be understood by the skilled artisan. For example, in some embodiments, the stereoisomerization step is mediated by a suitable catalyst, in particular a metal catalyst. However, other catalysts capable of facilitating the non-specific stereoisomerization of inositol may be of use in the methods as described herein and fall within the scope of the methods. Examples of suitable metal catalysts include palladium, platinum, ruthenium, rhodium, and nickel. The metal catalyst may be in the form of the neutral metal, or may be in the form of suitable metal alloy, oxide, salt, or organometallic species. Preferably, the catalyst is nickel or an activated nickel species, such as, for example, sponge nickel or Raney nickel. Most preferably, the catalyst is sponge nickel. Suitable catalysts are available commercially, e.g., from W.R. Grace & Co., Johnson Matthey, or from other commercial suppliers.

The catalyst used in the non-specific stereoisomerization step may be employed in any amount effective to catalyze the reaction. In some embodiments, the catalyst is present in amounts of no more than 100% (w/w inositol). In other embodiments, the catalyst is present at no more than 85% (w/w inositol). In still other embodiments, the catalyst is present at no more than 70% (w/w inositol) or is present at even lower levels. In some embodiments, sponge nickel catalyst is used in an amount of about 70-100% (w/w inositol), also about 70-90% (w/w inositol), also about 75-90% (w/w inositol). In some embodiments, such as those utilizing activated nickel catalysts, the reaction may be carried out under hydrogen atmosphere. In preferred embodiments, the catalyst is removed from the mixture prior to the conversion of the scyllitol to scyllitol diborate, for example, the mixture can be filtered (e.g. through Celite) at elevated temperature (e.g. 50-95° C., also 70-95° C., also 85-95° C.) to remove the catalyst. In some embodiments, the filtered catalyst can be rinsed with water and the filtrate added to the reaction mixture prior to conversion of scyllitol to scyllitol diborate.

In some embodiments, the non-specific stereoisomerization step is performed at a temperature above ambient temperature and is performed for extended periods of time. For example, the reaction may be usefully performed at greater than 50° C. for at least 30 minutes. In some embodiments, the reaction is performed at greater than 60° C., greater than 70° C., or even greater than 80° C. In some embodiments, the reaction is performed for at least 1 hour, at least 2 hours, or even at least 3 hours. In preferred embodiments the reaction is performed at about 90-100° C., also about 95-100° C. for at least 3 hours, although other times and temperatures may be suitably employed in the practice of the methods as described herein.

The pH of the solution used in the non-specific stereoisomerization step may also affect the rate and efficiency of the reaction and may additionally affect the levels of contaminants remaining in the products of the reaction. In some embodiments, the stereoisomerization step is performed at a basic pH. In some embodiments, the stereoisomerization step is performed at pH 8-12. In some embodiments, the stereoisomerization step is performed at pH 10-11. In some embodiments, the stereoisomerization step is performed at pH 8-11, also pH 8-10. In preferred embodiments, the step is performed at pH 8-9. In a preferred embodiment, the mixture of inositol and sponge nickel in water is at sufficiently high pH, and no adjustment of the pH is required.

In some embodiments, the non-specific stereoisomerization step is performed in an aqueous solution, preferably in about 4-8 volumes, also about 5-7 volumes, also about 6 volumes of water (w/w inositol). In some embodiments, the stereoisomerization step is performed in 4-8 volumes, also 5-7 volumes, also 6 volumes of water with about 70-100%, also about 70-90%, also about 75-90% sponge nickel catalyst at above ambient temperatures, preferably at about 90-100° C., or about 95-100° C. In some embodiments, the stereoisomerization is performed at about 90-100° C., or about 95-100° C. for about 1 hour, about 1-2 hours, about 1-3 hours, about 1-4 hours, or about 1-5 hours. In some embodiments, after the stereoisomerization and prior to conversion of the scyllitol to scyllitol diborate, the mixture is filtered to remove the nickel catalyst, for example by filtering through Celite®. The mixture is preferably filtered at about 70-95° C., also about 85-95° C. In some embodiments, the filtered nickel catalyst is rinsed with water, and the resulting filtrate is combined with the reaction filtrate. In some embodiments, the catalyst is rinsed with about 1-3 volumes, also about 2 volumes of water at about 50-60° C. In some embodiments, the stereoisomerization comprises the steps of i) combining inositol, preferably myo-inositol, sponge nickel and about 4-8 volumes of water (w/w inositol) in a reaction vessel, thereby providing a mixture; ii) heating the mixture to about 95-100° C.; iii) cooling the mixture to about 85-95° C. and filtering the mixture to remove the sponge nickel from filtrate; iv) rinsing the reaction vessel with about 1-3 volumes of water at about 50-60° C.; v) filtering the rinse through the filtered nickel at about 50-60° C.; and vi) combining the filtrate from step iii) and the rinse from step v) to provide a second mixture. In some embodiments, the mixture is heated to about 95-100° C. for about 1-5 hours, also 1-4 hours, also 1-3 hours in step ii). In some embodiments, about 6 volumes of water are used in step i), and 75-90% (w/w inositol) sponge nickel is used. In some embodiments, 2 volumes of water are used in step iv).

In some embodiments, inositol, preferably myo-inositol, is combined with a metal catalyst, preferably sponge nickel, more preferably about 75-90% (w/w inositol) sponge nickel, in water, preferably about 6 volumes of water (w/w inositol) and the mixture is heated, preferably to about 95-100° C., preferably over about 1-3 hours. The mixture is cooled, preferably to about 85-95° C. and filtered to remove the catalyst. The reaction vessel is optionally rinsed, preferably with about 2 volumes of water, and the rinse is filtered through the filtered catalyst, preferably at about 50-60° C. The original filtrate and optional rinse can be combined and used in the conversion of scyllitol to scyllitol diborate.

The methods as described herein comprise the step of conversion of scyllitol from the stereoisomerization of inositol to scyllitol diborate. Scyllitol diborate, which is relatively insoluble, may then be readily isolated from the mixture in substantially pure form. The specific method of converting scyllitol to scyllitol diborate is not critical to the methods described herein, and can be effected, for example, by reaction with a suitable source of borate at high pH, for example boric acid, or sodium tetraborate at pH of about 8-12, also about 8-11, also about 9-10. In preferred embodiments, however, the conversion comprises reaction of the scyllitol present in the mixture of inositol isomers with sodium tetraborate ($Na_2B_4O_7$) to generate scyllitol diborate. The skilled artisan would appreciate that other reagents may usefully generate scyllitol diborate from scyllitol and would therefore also be suitable for use in the methods as described herein.

In order to avoid contamination of the final product with boron, it may be desirable to use no more reagent than necessary to effect the conversion of scyllitol to scyllitol diborate. For example, in some embodiments, no more than about 4 equivalents of boron relative to scyllitol are provided for the conversion reaction. In some embodiments, no more than about 3 equivalents of boron relative to scyllitol are provided. In preferred embodiments, no more than about 2 equivalents of boron relative to scyllitol are provided. The amount of sodium tetraborate used in the conversion reaction may alternatively be expressed relative to the amount of inositol used in the non-specific stereoisomerization reaction. For example, in some embodiments, no more than about 1.6 equivalents of boron relative to inositol are provided for the conversion reaction. In some embodiments, no more than about 1.2 equivalents of boron relative to inositol are provided. In preferred embodiments, no more than about 0.8 equivalents of boron relative to inositol are provided (e.g. about 0.2 equivalents of $Na_2B_4O_7$ relative to inositol). In some embodiments, about 0.15-0.5, also about 0.15-0.3, or about 0.2 equivalents of $Na_2B_4O_7$ relative to inositol are used.

The conversion of scyllitol to scyllitol diborate by reaction with sodium tetraborate ($Na_2B_4O_7$) is preferably performed at elevated temperature for appropriate times. For example, the reaction may be usefully performed at greater than 50° C. for at least 30 minutes. In some embodiments, the reaction is performed at greater than 60° C., greater than 70° C., or even greater than 80° C. In some embodiments, the reaction is performed for at least 45 minutes, at least 1 hour, or even at least 1.5 hours. In preferred embodiments the reaction is performed at about 75-95° C., also about 80-90° C., also about 80-85° C. for about 1-5 hours, also about 1-3 hours, also about 1-1.5 hours, although other times and temperatures may be suitably employed in the reaction. In some embodiments, the conversion of scyllitol to scyllitol diborate with sodium tetraborate ($Na_2B_4O_7$) is preferably performed at elevated pH, for example at pH about 8-11, preferably pH about 9-10. In some embodiments, the mixture of scyllitol from the stereoisomerization of inositol is combined with $Na_2B_4O_7$ and the mixture is heated to about 65-95° C., also about 75-95° C., also about 80-85° C., preferably about 80-90° C. and base, preferably NaOH, is added until the mixture is at pH about 8-11, preferably pH about 9-10. In preferred embodiments the mixture at pH of about 8-11, preferably pH about 9-10 is heated at about 75-95° C., preferably about 80-90° C., for about 1-5 hours, also about 1-3 hours, also about 1-1.5 hours. In some embodiments, the conversion of scyllitol to scyllitol diborate comprises the steps of vii) combining the second mixture from step vi) of the stereoisomerization process (see paragraph [0178]) with $Na_2B_4O_7$ in a second reaction vessel to provide a third mixture; viii) heating the third mixture to about 80-90° C.; ix) adding base, preferably NaOH, to the third mixture to bring the pH to within the range of about 9-10; x) stirring the third mixture at pH about 9-10 at about 80-90° C.; xi) cooling the third mixture to about 20-30° C.; xii) agitating the third mixture at about 20-30° C. to provide a slurry; xiii) filtering the slurry to isolate scyllitol diborate from inositol recovery filtrate; xiv) optionally rinsing the second reaction vessel with about 0.5 to 2 volumes of water and filtering the rinse through the solid scyllitol diborate; and xv) optionally repeating step xiv). In some embodiments, about 0.15-0.3, also about 0.2 equivalents of $Na_2B_4O_7$ are used in step vii). In some embodiments, the mixture is heated to about 80-90° C. over 2-3 hours in step viii). In some embodiments, NaOH is added to the third mixture over about 5-10 minutes in step ix). In some embodiments the third mixture is stirred for about 1 hour at about 80-90° C. at about pH 9-10 in step x). In some embodiments, the third mixture is cooled to 20-30° C. over about 4-16 hours in step xi). In some embodiments, the third mixture is agitated at about 20-30° C. for at least 1 hour in step xii). In some embodiments, the second reaction vessel is rinsed with about 1 volume of water in step xiv), and optionally in step xv). In some embodiments, the mixture is cooled to 20-30° C. In some embodiments, the mixture is agitated at 20-30° C. In some embodiments, the mixture is cooled to 20-30° C. for 1-20 hours, also 1-16 hours, also 4-16 hours, and then agitated at 20-30° C. In some embodiments, the mixture is agitated for at least 1 hour, also 1-3 hours, also 1-2 hours, also about 1 hour. The resulting scyllitol diborate precipitate is isolated from the mixture by methods known in the art for separating a solid precipitate mixed with a liquid. For example, the scyllitol diborate precipitate is isolated by decantation, centrifugation, precipitation, or the like. In a preferred embodiment, scyllitol diborate is isolated by filtering the mixture. In some embodiments, the resulting solid is washed with water. The resulting mixture (e.g. solution, supernatant, filtrate) recovered from the isolation of scyllitol diborate (with or without added solution from washing the solid scyllitol diborate), is also referred to as inositol recovery mixture, inositol recovery solution, inositol recovery supernatant, or inositol recovery filtrate, may be recycled by using it in a repeat of the stereoisomerization step as described herein.

The methods as described herein further comprise the step of isolation of the scyllitol diborate from the mixture. As previously mentioned, scyllitol diborate is relatively insoluble in aqueous solution, and the product of the conversion reaction may therefore, in some embodiments, be isolated from the mixture by precipitation and recovery of the precipitated material by conventional methods, for example by decantation, centrifugation, filtration or the like. In preferred embodiments, the scyllitol diborate may be isolated from the solution by filtration. In order to minimize contamination of the isolated scyllitol diborate by boron or other water-soluble contaminants, it may be desirable to wash the isolated material, for example by slurrying the precipitate in water. The washing step may also remove undesirable inositol isomers from the precipitated scyllitol diborate. The isolated, and optionally washed, scyllitol diborate may be further dried if desired, for example by heating at 45-55° C. Alternatively, the solid scyllitol diborate may be dried at even higher temperatures, such as, for example 80-85° C. or even 115-120° C., without causing decomposition of the isolated scyllitol diborate product. Such drying may allow easier handling of the scyllitol diborate and may minimize microbial growth in the isolated material during storage. The resulting mixture (e.g. solution, supernatant, filtrate) recovered from the isolation of scyllitol diborate (with or without added solution from washing the solid scyllitol diborate), also referred to as inositol recovery mixture, inositol recovery solution, inositol recovery supernatant or inositol recovery filtrate, may be recycled by using it in a repeat of the stereoisomerization step as described herein. Additional inositol (preferably myo-inositol) may be added to the inositol recovery mixture prior to repeating the stereoisomerization step. The recycling of this solution provides additional scyllitol diborate that can be converted to substantially purified scyllitol, thereby improving the yield of the overall process.

The yields of scyllitol diborate obtained in the methods as described herein may vary depending on the conditions used for the various steps. In some embodiments, the overall yield of scyllitol diborate is at least 20%, 25%, 30%, 35%, or 40%. In some embodiments, the overall yield of scyllitol diborate may be even higher.

In another aspect, novel methods of chemical synthesis are provided, comprising the steps of non-specific stereoisomerization of a solution of inositol, conversion of scyllitol in the solution to scyllitol diborate, isolation of the scyllitol diborate from the solution, and conversion of the isolated scyllitol diborate to scyllitol. The steps of non-specific stereoisomerization, conversion of scyllitol in the solution to scyllitol diborate, and isolation of the scyllitol diborate may be carried out as described above.

The conversion of isolated scyllitol diborate to scyllitol may be performed by any suitable method. In some embodiments, the conversion step comprises a hydrolysis reaction. In specific embodiments, the hydrolysis reaction is mediated by a catalyst. In preferred embodiments, the catalyst is an acid, such as, for example, a mineral acid such as hydrochloric acid, sulfuric acid, nitric acid, or phosphoric acid, although other agents may usefully catalyze the hydrolysis of scyllitol diborate to scyllitol. Preferably sulfuric acid or hydrochloric acid, preferably hydrochloric acid is used to catalyze the hydrolysis of scyllitol diborate to scyllitol.

In some embodiments, the conversion of isolated scyllitol diborate to scyllitol may be performed at high temperature and/or for extended periods of time. The relative volume of aqueous solution used in the reaction may also be varied as desired within the scope of the invention. For example, the reaction may be usefully performed at greater than 50° C. for at least 30 minutes. In some embodiments, the reaction is performed at greater than 60° C., greater than 70° C., greater than 80° C., or even greater than 85° C. In some embodiments, the reaction is performed at a temperature in the range of about 75-95° C., preferably about 85-95° C. In some embodiments, the reaction is performed for at least 45 minutes, at least 1 hour, or even at least 1.5 hours. In some embodiments, the reaction is performed for about 1-5 hours, also about 1-3 hours, also about 1.5-3 hours, also about 1.5-2.5 hours, also about 2-3 hours. In some embodiments, the hydrolysis reaction is performed in at least one volume of aqueous solution, at least two volumes of aqueous solution, at least five volumes of aqueous solution, or even larger volumes of aqueous solution. In some embodiments, the reaction is performed in about 6-14 volumes, also about 8-12 volumes, also about 10 volumes of about 0.5-2 N acid, also about 0.5-1.5 N acid, preferably about 1N acid, where preferably the acid is HCl. In preferred embodiments, the conversion reaction is performed in about 10 volumes of about 1 N HCl at about 85-95° C. for about 1.5-2.5 hours.

In some embodiments, the conversion reactions may be monitored to assess the progress of the reaction. Such monitoring may be performed, for example, by measurement of the pH of the solution, as acid is consumed during the hydrolysis reaction. In some embodiments, the conversion of isolated scyllitol diborate to scyllitol is monitored by chromatographic or spectroscopic techniques, such as, for example, by $^1$H NMR or by other suitable techniques. In preferred embodiments, the conversion of isolated scyllitol diborate to scyllitol is monitored by the measurement of pH. In some embodiments, the conversion of isolated scyllitol diborate to scyllitol is considered complete if the pH of the solution following the reaction is less than 2.0, less than 3.0, less than 4.0, or less than 5.0. In preferred embodiments, the conversion of isolated scyllitol diborate to scyllitol is considered complete if the pH of the solution following the reaction is less than 2.0.

Following the conversion reaction, scyllitol may be isolated from the solution using any suitable method. In some embodiments, the dissolved scyllitol may be isolated directly from the solution by chromatographic or other suitable methods. In some embodiments, the dissolved scyllitol may be precipitated or crystallized prior to the isolation. For example, the resulting mixture after converting scyllitol diborate to scyllitol may be cooled, preferably to about 20-30° C., preferably over about 3-4 hours, and then agitated at about 20-30° C., preferably for about 1-2 hours. Substantially pure scyllitol can be isolated from the resultant slurry. In some embodiments, the scyllitol produced by conversion of isolated scyllitol diborate is isolated by crystallization.

The solid scyllitol product may be usefully separated from the liquid phase by any suitable method, for example by centrifugation or filtration. In preferred embodiments, the solid scyllitol is isolated by filtration. Those of ordinary skill in the art would understand, however, that other methods of separation of the reaction product from the liquid phase may be employed in the process and would fall within the scope of the invention. In preferred embodiments, the solid scyllitol product is washed following its isolation from the liquid phase.

As noted above, the solution remaining after the initial isolation of scyllitol diborate (i.e. inositol recovery mixture) may usefully be recycled in order to increase yields of product. In a similar manner, it may in some cases be desirable to repeat the steps of the method on solution remaining after conversion of the isolated scyllitol diborate to scyllitol and isolation of scyllitol from the solution. The resulting solution is referred to as diborate recovery mixture, diborate recovery solution, diborate recovery supernatant, or diborate recovery filtrate. This diborate recovery solution can be reacted to form scyllitol diborate, which can be isolated by methods as described above. The recovered scyllitol diborate can then be treated by the steps of the methods described above for forming scyllitol from scyllitol diborate. In some embodiments, the steps are repeated on a recovered scyllitol diborate sample at least 1, 2, 3, 4, 5, 6, 7, 8, 9, 10, 15 or even more times, for example one batch of recovered scyllitol diborate sample converted to scyllitol is a first repeat of the steps, a second recovered scyllitol diborate sample converted to scyllitol is a second repeat of the steps, and so forth. In order to be clear on the scope of the recovery/recycling process, for an initial reaction of inositol taken through the steps of stereoisomerization, conversion of scyllitol to scyllitol diborate, isolation of the scyllitol diborate, and conversion to scyllitol, the diborate recovery solution resulting from isolation of the scyllitol as a solid is a first diborate recovery solution. Similarly, if scyllitol diborate is obtained from any other process not involving a diborate recovery solution, and is converted to scyllitol and the scyllitol isolated, the resulting diborate recovery solution is a first diborate recovery solution. This first diborate recovery solution can be recycled to form a first recovered scyllitol diborate, and can be converted to scyllitol with isolation of the scyllitol, with the resulting diborate recovery solution from this step being a second diborate recovery solution. The second diborate recovery solution converted to a second recovered scyllitol diborate, to scyllitol and isolation of the scyllitol results in a third diborate recovery solution, and so forth. Without limitation, the recovered scyllitol diborate sample that is used in the recycling process could be any combination of recovered scyllitol diborate, for example a combination of two or more batches of first recovered scyllitol diborate, a combination of a first recovered scyllitol diborate and a second recovered scyllitol diborate, and so forth, or could even be a combination of recovered scyllitol diborate and scyllitol diborate that has not gone through this recycling process. The improvement in yield can be gained by just one recycling, i.e. converting one batch of a first recovery diborate solution through the steps to scyllitol. In a preferred embodiment, the recycling step is performed on at least two batches of first recovery diborate solutions.

In another aspect, methods of improving a process for the preparation of scyllitol are provided, wherein the improvement can be applied to any process comprising the step of forming scyllitol from scyllitol diborate. A variety of processes involve the formation of scyllitol in a mixture comprising impurities, such as other isomers of inositol. For example the non-specific stereoisomerization of a solution of myo-inositol; the reduction of a solution of hexahydroxybenzene with Raney nickel; a bioconversion process of a solution of myo-inositol to produce scyllitol, and/or scyllo-inosose, optionally further comprising reacting the scyllo-inosose to form additional scyllitol, all provide scyllitol that needs to be purified from the mixture. One known method to purify scyllitol from such mixtures is to form a diborate complex of the scyllitol, which can be readily precipitated from the mixture, as described above, for example, to isolate the scyllitol diborate from impurities. The isolated scyllitol diborate can then be reacted to form scyllitol, which can be isolated in substantially pure form. Thus, any of a variety of know processes for the preparation of substantially pure scyllitol, that may involve the formation of scyllitol diborate as part of the process, can be improved by methods as provided herein. The provided method comprises the conversion of isolated scyllitol diborate to substantially purified scyllitol, isolation of the scyllitol, for example by filtration, and recycling of the remaining solution (e.g. supernatant, or filtrate where scyllitol is collected by filtration) to form recovered scyllitol diborate, which can be converted to additional scyllitol, thereby improving the overall yield of scyllitol. The filtrate is optionally combined with filtrates from the aqueous washing of the filtered scyllitol. Such a filtrate or supernatant is referred to as a diborate recovery supernatant (or diborate recovery filtrate, diborate recovery solution, or diborate recovery mixture), and can be converted back to scyllitol diborate.

In some embodiments, the recovered diborate mixture is converted to scyllitol diborate by heating the mixture, adding base to provide a basic aqueous mixture, and precipitating scyllitol diborate from the mixture. In some embodiments, the recovered diborate mixture is converted to scyllitol diborate by following the steps of i) heating the mixture; ii) adjusting the pH of the mixture to about 9-10; and iii) precipitating scyllitol diborate from the mixture. In some embodiments, diborate recovery mixture can be converted back to the scyllitol diborate by following the steps of i) heating the mixture, preferably to about 80-90° C.; ii) adding base to provide a pH of the mixture of about 9-10; iii) cooling the mixture to provide a scyllitol diborate precipitate; and iv) agitating the cooled mixture to provide a slurry. In some embodiments, diborate recovery mixture can be converted back to the scyllitol diborate by following the steps of i) heating the mixture to about 80-90° C.; ii) adding base to provide a pH of the mixture of about 9-10; iii) cooling the mixture, preferably to about 20-30° C. to provide a scyllitol diborate precipitate; and iv) agitating the cooled mixture, preferably at about 20-30° C., to provide a slurry. In some embodiments, diborate recovery mixture can be converted back to the scyllitol diborate by following the steps of i) heating the mixture to about 80-90° C.; ii) adding base to provide a pH of the mixture of about 9-10; iii) cooling the mixture to about 20-30° C.; and iv) agitating the mixture to provide a slurry comprising scyllitol diborate precipitate. The desired scyllitol diborate can be isolated as a solid from the resulting slurry by methods known in the art for separating a solid precipitate mixed with a liquid, for example decantation, centrifugation, precipitation, or the like, preferably by filtration. In some embodiments, diborate recovery mixture can be converted back to the scyllitol diborate by following the steps of i) heating the mixture; ii) adjusting the pH of the mixture to about 9-10; iii) precipitating scyllitol diborate from the mixture; and iv) isolating scyllitol diborate as a solid. In some embodiments, diborate recovery mixture can be converted back to the scyllitol diborate by following the steps of i) heating the mixture to about 80-90° C.; ii) adding base to provide a pH of the mixture of about 9-10; iii) cooling the mixture to provide a scyllitol diborate precipitate; and iv) isolating scyllitol diborate as a solid.

In some embodiments, diborate recovery mixture can be converted back to the scyllitol diborate by following the steps of i) heating the mixture to about 80-90° C.; ii) adding base to provide a pH of the mixture of about 9-10; iii) cooling the mixture to about 20-30° C.; iv) agitating the cooled mixture at about 20-30° C. to provide a slurry comprising scyllitol diborate precipitate; and v) isolating scyllitol diborate as a solid. In some embodiments, diborate recovery mixture can be converted back to the scyllitol diborate by following the steps of i) heating the mixture to about 80-90° C. over about 2-3 hours; ii) adding NaOH to provide a pH of the mixture of about 9-10; iii) cooling the mixture to about 20-30° C. over about 3-4 hours; iv) agitating the mixture at about 20-30° C. for at least 1 hour to provide a slurry comprising scyllitol diborate precipitate; and v) filtering the slurry to provide scyllitol diborate as a solid. The resulting diborate recovery mixture from step v) can be similarly recycled. In some embodiments, diborate recovery mixture can be converted back to the scyllitol diborate by following the steps of i) heating the mixture; ii) adjusting the pH of the mixture to pH about 9-10; iii) precipitating scyllitol diborate by cooling the mixture; iv) agitating the cooled solution to provide a slurry; and iv) isolating scyllitol diborate as a solid.

In some embodiments, a method of preparing substantially pure scyllitol is provided, comprising the steps of: i) heating a mixture of scyllitol diborate in aqueous acid, preferably about 1N HCl, preferably heating to about 85-95° C. in a reaction vessel; ii) agitating the mixture at high temperature, preferably at about 85-95° C. to obtain a solution; iii) cooling the solution, preferably to about 20-30° C.; iv) agitating the solution, preferably at about 20-30° C. to provide a slurry; v) filtering the slurry to isolate substantially pure scyllitol solid from a diborate recovery filtrate; vi) optionally rinsing the reaction vessel with about 0.5-2 volumes of water and filtering the rinse through the substantially pure scyllitol solid; and vii) optionally repeating step vi). The resulting diborate recovery filtrate can be recycled, following the steps of: viii) heating the diborate recovery filtrate from step v), optionally combined with the rinse(s) from steps vi) and vii), preferably to about 80-90° C. in a second reaction vessel; ix) adding base to the diborate recovery filtrate, preferably NaOH, to bring the pH to within the range of about 9-10, thereby forming a second mixture; x) agitating the second mixture at high temperature, preferably at about 80-90° C.; xi) cooling the second mixture, preferably to about 20-30° C.; xii) agitating the second mixture, preferably at about 20-30° C. to provide a second slurry; xiii) filtering the second slurry to isolate recovered scyllitol diborate solid from additional diborate recovery filtrate; xiv) optionally rinsing the second reaction vessel with about 0.5-2 volumes of water, preferably about 1 volume of water, and filtering the rinse through the recovered scyllitol diborate solid; xv) optionally repeating step xiv); xvi) recycling the recovered scyllitol diborate solid through steps i) through vii) to provide additional substantially pure scyllitol solid and additional diborate recovery filtrate; and xvii) optionally combining the substantially pure scyllitol solids from steps v) and xvi). In some embodiments, the scyllitol diborate used in step i) is isolated from step xiii), or can be from any batch of optionally rinsed recovered scyllitol diborate as described herein (i.e can be a recovered scyllitol diborate as prepared by this method. In some embodiments, the scyllitol diborate used in step i) is recovered scyllitol diborate as described herein. In some embodiments, the scyllitol diborate used in step i) is isolated from any process involving purification of scyllitol by forming scyllitol diborate.

The yields of scyllitol obtained in the methods as described herein may vary depending on the conditions used for the various steps. In some embodiments, the overall yield of scyllitol is at least 20%, 25%, 30%, 35%, or 40%.

The methods provided herein offer the additional advantage of producing products on a large scale of high purity, e.g. suitable for use in humans. In particular, the scyllitol diborate and scyllitol produced according to the instant methods contain relatively low levels of impurities, despite the high efficiencies of the synthetic methods. In some embodiments, the methods provide scyllitol that contains no more than 100 ppm of nickel, or aluminum. In some embodiments, the methods provide scyllitol that contains no more than 50 ppm of nickel, or aluminum. In preferred embodiments, the methods provide scyllitol that contains no more than 20 ppm nickel, or aluminum. In highly preferred embodiments, the methods provide scyllitol that contains no more than 20, also 10, also 5, also 3 ppm nickel. In other highly preferred embodiments, the methods provide scyllitol that contains no more than 50, also 30, also 20, also 10, also 5 ppm aluminum. In still other embodiments, the methods provide scyllitol that contains no more than about 300 ppm, also about 200 ppm, also about 100 ppm, or about 60 ppm boron. Such low levels of impurities are achieved in samples using the recovery and recycling methods as described herein, for example using recycling of inositol recovery mixture and using recycling of recovered diborate from diborate recovery mixture.

It will be readily apparent to one of ordinary skill in the relevant arts that other suitable modifications and adaptations to the methods and applications described herein may be made without departing from the scope of the invention or any embodiment thereof. Having now described the present invention in detail, the same will be more clearly understood by reference to the following Examples, which are included herewith for purposes of illustration only and are not intended to be limiting of the invention.

EXAMPLES

The following examples are used to illustrate the methods as described herein, and refer to batches within the process, where these batches are understood to be internal batches within the process with our without the steps of recycling. The overall process from one lot, or batch of starting material to the final amount of recovered scyllitol represents a final batch of substantially pure scyllitol, where the internal batches (e.g. subset batches) within a process may be combined to form a final batch of scyllitol. Overall yields and amounts of scyllitol are based on the final batch (e.g. combination of internal batches, or subset batches), whether or not the process includes the recycling steps as described herein.

Synthesis of Scyllitol from Myo-Inositol Using an All-Aqueous Process with Recycled Filtrates Scyllitol has been efficiently prepared from myo-inositol according to the scheme shown below:

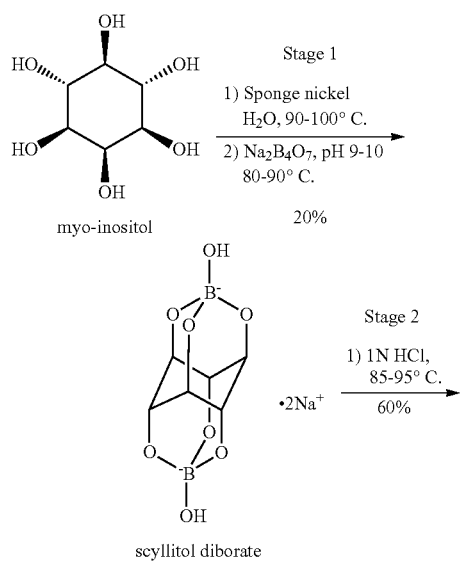

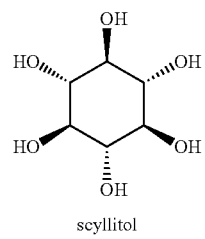

scyllitol

It was discovered that the overall yield of the process could be increased significantly by recycling the solution remaining after isolation of the insoluble scyllitol diborate and subjecting that solution (i.e. inositol recovery solution), optionally with added myo-inositol, to additional rounds of isomerization and diborate formation, for example as shown in FIG. 1.

FIG. 2 shows a batch tree with predicted yields for a process consisting of six batches of diborate in which each subsequent batch uses the diborate filtrate (i.e. diborate recovery filtrate) from the previous diborate preparation. In addition, 38.4% of the initial myo-inositol charge is added to the diborate batches using recycled filtrate. Seven amounts (total) of scyllitol were prepared using an all-aqueous isolation followed by the recovery of scyllitol from the filtrates by conversion to the diborate. The reactions were primarily executed in 12-L and 22-L jacketed reactors.

Methods

Preparation of Scyllitol Diborate

The first step for the preparation of scyllitol diborate involves a sponge nickel mediated isomerization of myo-inositol in water near reflux to yield a mixture of inositols consisting of roughly 22% scyllitol (as judged by HPLC). After separating the crude reaction mixture from the nickel, scyllitol is selectively converted to scyllitol diborate by treatment with sodium tetraborate at 80-90° C. and pH 9-10. Scyllitol diborate is then crystallized by cooling and is isolated in 17-20% yield and >99% HPLC purity (AUC). All six batches of diborate proceeded as expected (Table 1). The isomerization reactions required 2-3 hours to heat to 95-100° C. and each were sampled for analysis after 1, 2, and 3 hours. All five reactions resulted in myo/scyllo ratios of 2-3:1 (typical) by $^1$H NMR and all but one batch resulted in >20% AUC (HPLC Analysis) scyllo-inositol (Table 2). The diborate formations resulted in myo/scyllo ratios of >60:1 (typical) by $^1$H NMR (Table 2) within one hour and the subsequent crystallizations were allowed to proceed over 14-16 hours (overnight). The resulting diborate slurries filtered very fast and were isolated as large white crystals. The diborate filter cakes were found to have consistent $^1$H NMR spectra, HPLC purities of 98.7%-99.2% AUC and moisture levels of 46.8%-56.4%. Nickel and aluminum analysis revealed levels ranging from <1 ppm to 17 ppm for nickel and <1 ppm to 28 ppm for aluminum. The yields corrected for moisture content ranged from 17.1% to 20.3%.

TABLE 1

Production Summary for the Preparation of Scyllitol Diborate

| Batch | Yield (%)[a] | % H$_2$O | HPLC (% AUC)[b] | Ni and Al (ppm) | $^1$H NMR |
|---|---|---|---|---|---|
| 1 | 390 g (18.3%) | 49.80 | 98.90 | Ni: 1, Al: 28 | Consistent |
| 2 | 409 g (20.3%) | 46.80 | 99.10 | Ni: 6, Al: 3 | Consistent |
| 3 | 438 g (19.2%) | 53.10 | 99.20 | Ni: <1, Al: <1 | Consistent |
| 4 | 420 g (17.1%) | 56.40 | 99.20 | Ni: 17, Al: 3 | Consistent |

TABLE 1-continued

Production Summary for the Preparation of Scyllitol Diborate

| Batch | Yield (%)[a] | % H$_2$O | HPLC (% AUC)[b] | Ni and Al (ppm) | $^1$H NMR |
|---|---|---|---|---|---|
| 5 | 405 g (19.5%) | 48.60 | 98.90 | Ni: 2, Al: 3 | Consistent |
| 6 | 436 g (19.8%) | 51.50 | 98.70 | Ni: 2, Al: 4 | Consistent |

[a]Diborate outputs are reported as filter-cake weights with yields that have been corrected for moisture content.

TABLE 2

Results for the Preparation of Diborate

| | Isomerization, myo/scyllo (HPLC Results, % scyllo) | | | Diborate Formation myo/scyllo | |
|---|---|---|---|---|---|
| Batch | 1 | 2 | 3 | 1 | 2 |
| 1 | 13.7:1 (9.4%)[a] | 3.2:1 (21.5%) | 2.5:1 (24.0%) | 212:01:00 | na |
| 2 | 3.9:1 (15.9%) | 2.8:1 (19.6%) | 2.5:1 (20.8%) | 31:1[b] | 62:01:00 |
| 3 | 6.1:1 (9.7%) | 2.5:1 (14.4%) | 2.0:1 (15.8%) | 81:01:00 | na |
| 4 | 17.0:1 (19.5%) | 14.0:1 (22.6%) | 2.8:1 (24.0%) | 102:01:00 | na |
| 5 | 2.5:1 (20.6%) | 2.5:1 (23.3%) | 2.0:1 (23.9%) | 94:01:00 | na |
| 6 | 4.3:1 (17.3%) | 2.4:1 (22.6%) | 2.2:1 (24.0%) | 84:01:00 | na |

[a]Sampled at 83° C. before switching to a temperature-control module with a higher maximum temperature setting.
[b]Sampled after 15 minutes.

For quality-assurance purposes, it may be helpful to perform release testing on the diborate filtrates prior to the recycling. This release testing may, for example, be based on HPLC analysis of the filtrates. Table 3 reports the HPLC data for representative diborate filtrates. In general it appears that the levels of the minor unknown impurities appear to gradually increase while the levels of the major known impurities appear to gradually decrease. This is in agreement with the possibility that low-level impurities will gradually increase over time. The filtrates from the additional recycling on a 1/10-scale were also analyzed by HPLC to give a more complete picture of this phenomenon (Table 8). Based on these results it is expected that yields for the recycled filtrate of >37% of starting myo-inositol may be achieved.

TABLE 3

HPLC Data for Diborate Filtrates

| | | Batch (% Area) | | | | | |
|---|---|---|---|---|---|---|---|
| Name | t$_R$ (min) | 1 | 2 | 3 | 4 | 5 | 6 |
| | 7.9 | na | 0.51 | 0.64 | 0.75 | 0.75 | 0.82 |
| | 9.4 | na | 0.67 | 0.99 | 1.25 | 1.20 | 1.32 |
| | 10.4 | na | 4.85 | 6.12 | 7.48 | 9.12 | 8.70 |
| | 11.2 | na | 3.10 | 3.90 | 4.88 | 5.84 | 5.67 |
| | 15.4 | na | 0.55 | 0.57 | 0.64 | 0.66 | 0.65 |
| | 16.7 | na | 0.28 | 0.39 | 0.44 | 0.51 | 0.49 |
| | 17.4 | na | 0.39 | 0.43 | 0.50 | 0.56 | 0.52 |
| | 18 | na | 0.62 | 0.68 | 0.69 | 0.78 | 0.84 |
| allo-Inositol | 20 | 1.19 | 0.00 | 0.00 | 0.00 | 0.00 | 0.00 |
| | 21 | na | 1.64 | 1.89 | 2.15 | 2.33 | 2.46 |
| | 22.1 | na | 1.20 | 1.35 | 1.60 | 1.78 | 1.82 |
| | 22.8 | na | 1.58 | 1.76 | 2.04 | 2.12 | 2.27 |
| muco-Inositol | 25.1 | 0.51 | 3.52 | 3.29 | 3.01 | 2.94 | 3.00 |
| | 36 | na | 6.62 | 8.41 | 9.18 | 9.80 | 9.40 |
| chiro-Inositol | 36.9 | 18.82 | 19.96 | 18.75 | 18.22 | 16.65 | 17.25 |
| neo-Inositol | 39.2 | 5.97 | 9.27 | 8.18 | 7.48 | 7.05 | 7.23 |
| myo-Inositol | 49.6 | 66.79 | 45.22 | 42.64 | 39.67 | 37.90 | 37.55 |
| scyllo-Inositol | 53 | 0.00 | 0.00 | 0.00 | 0.00 | 0.00 | 0.00 |

Preparation of Scyllitol

The conversion of scyllitol diborate to scyllitol was accomplished via a hydrochloric acid mediated hydrolysis. The process generates two equivalents of sodium chloride and boric acid. The reaction was carried out in ten volumes of 1 N HCl at 85-95° C., followed by crystallization to yield scyllitol in 60-65% yield and >99.9% purity (HPLC).

The seven batches of scyllitol proceeded as expected. The hydrolysis reactions were heated to 85-95° C. over 1.5-2.5 hours and during this time the slurries became solutions. For all of the batches, the first analysis ($^1$H NMR after 10 min to 1 h) revealed no detectable levels of diborate (pH≈0.5). The batches were cooled to 20-30° C. over 3-4 hours and then agitated at 20-30° C. for 1-2 hours. The resulting scyllitol slurries filtered very fast and were isolated as large white crystals (92-95% solids). Vacuum drying was carried out at 75-80° C. and required less than 16 hours to reach <0.1% moisture (oven KF). The yields ranged from 57-66% and the material had consistent $^1$H NMR, IR, and XRPD data (Tables 4 and 5). Nickel and aluminum levels were low, and boron levels were consistently near 60 ppm. Additional data reported in Table 5 includes DSC, sodium levels, particle size, and residue on ignition (ROI).

A modification was made for batch 12 in an effort to reduce the residual boron levels (56-73 ppm for Batches 7-11). The previous batches utilized two filter-cake washes that initially were used to rinse the reactor. Since minimal product typically remained in the reactor after the first wash it was decided to apply the second wash directly to the filter cake. While this was only one experimental result, the boron level for batch 12 was the lowest observed.

TABLE 4

Production Summary for the Preparation of Scyllitol

| Batch | Output (%) | % $H_2O$ | HPLC[a] (% AUC) | Ni, Al and B (ppm) | $^1$H NMR | XRPD[b] |
|---|---|---|---|---|---|---|
| 7 | 169.0 g (63.0%) | <0.1 | >99.9 | Ni: 3, Al: 5, B: 61 | Consistent | Consistent |
| 8 | 165.6 g (65.4%) | <0.1 | >99.9 | Ni: 1, Al: <1, B: 58 | Consistent | Consistent |
| 9 | 155.3 g (57.2%) | <0.1 | >99.9 | Ni: 1, Al: <1, B: 56 | Consistent | Consistent |
| 10 | 164.0 g (62.4%) | <0.1 | >99.9 | Ni: <1, Al: 3, B: 58 | Consistent | Consistent |
| 11 | 50.1 g (65.9%) | <0.1 | >99.9 | Ni: 1, Al: 2, B: 73 | Consistent | Consistent |
| 12 | 14.1 g (64.3%) | <0.1 | >99.9 | Ni: <1, Al: 3, B: 42 | Consistent | Consistent |
| 13 | 4.0 g (60.0%) | <0.1 | >99.9 | Ni: 2, Al: 5, B: 53 | Consistent | Consistent |

[a]Scyllitol was analyzed using the release HPLC method.
[b]XRPD patterns were consistent with the patterns observed in previous work.

TABLE 5

Additional Characterization of Scyllitol Batches

| Batch | ROI | Na | IR | DSC (Onset/ Peak, °C.) | Particle Size (μm)[a] | | |
|---|---|---|---|---|---|---|---|
| | | | | | $X_{10}$ | $X_{50}$ | $X_{90}$ |
| 7 | >0.1% | 15 ppm | Consistent | 357.9/361.2 | 149 | 270 | 437 |
| 8 | >0.1% | 18 ppm | Consistent | 357.6/361.1 | 161 (177) | 336 (473) | 575 (978) |
| 9 | >0.1% | 14 ppm | Consistent | 357.9/362.7 | 184 (423) | 362 (663) | 596 (1054) |
| 10 | >0.1% | 12 ppm | Consistent | 357.7/359.8 | 220 (209) | 381 (349) | 582 (569) |
| 11 | >0.1% | 15 ppm | Consistent | 357.6/360.0 | 233 | 449 | 664 |
| 12 | >0.1% | 26 ppm | Consistent | 358.0/361.0 | 49 | 104 | 183 |
| 13 | 0.10% | 53 ppm | Consistent | 357.1/360.7 | 49 | 118 | 202 |

[a]The high-end particle-size data (≈$X_{95}$) for batches 8 and 9 were above 900 μm which is outside the acceptable accuracy range for the instrument used. Samples from batches 8-10 were also sent to Particle Technology Labs (Downers Grove, IL) for particle-size analysis. PTL results are in parentheses.

Figure 4:
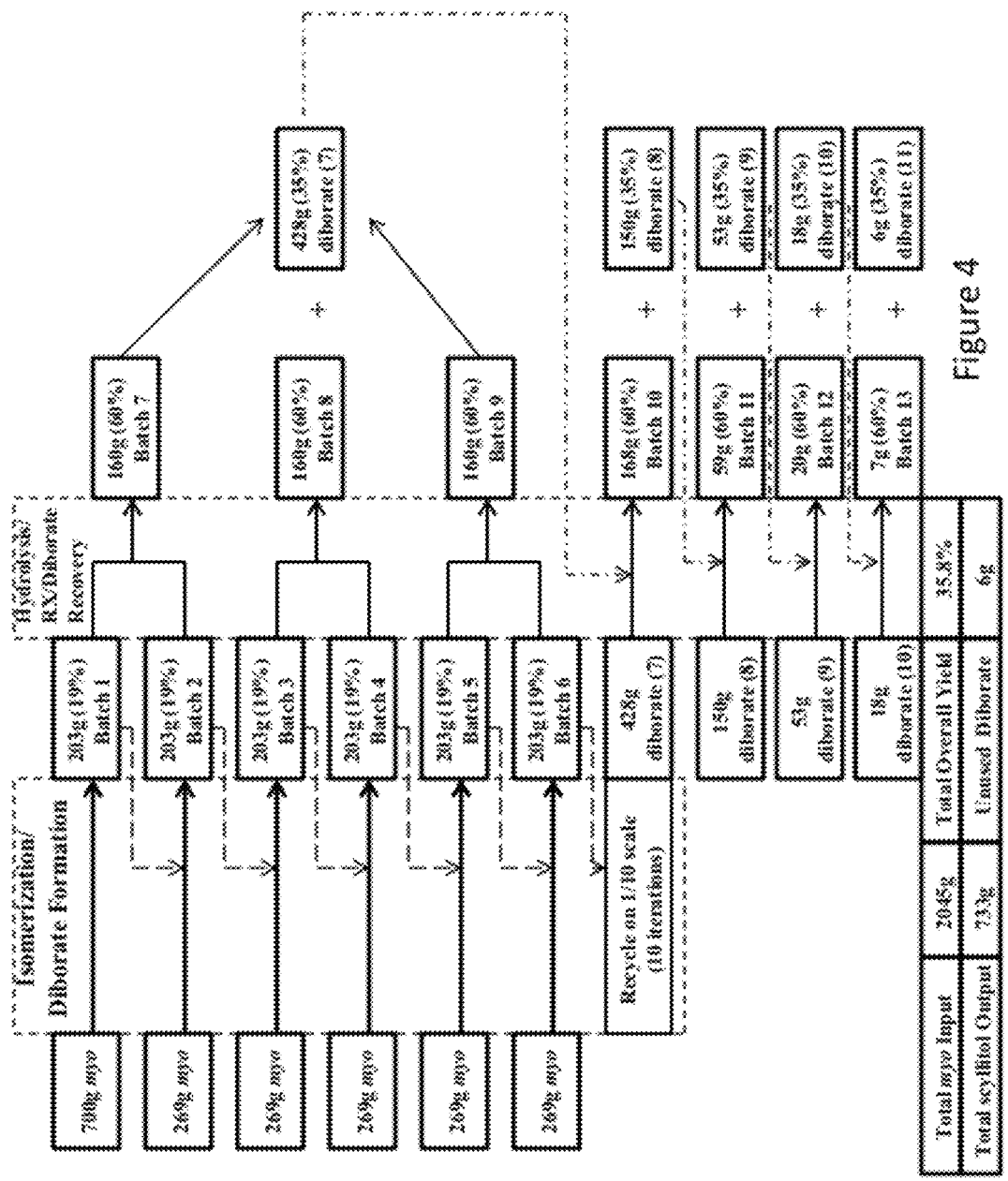
FIG. 4. Process for the synthesis of scyllitol from myo-inositol with corrected diborate yields. The raw material charges and predicted yields (both step-wise and overall) are shown after correction for the actual overall yield for Stage 1 (isomerization/diborate formation).

With all of the yields in hand from the preparation of scyllitol batches, it is noteworthy that the final scyllitol output of 722.3 g (35.3%) was 2.3% less than the predicted output of 769 g (37.6%, FIG. 2). This difference could be accounted for by substituting the actual overall yield (19%) for Stage 1 in place of the predicted Stage 1 yield for diborate (20%). With this substitution in place, a total scyllitol output of 733 g (35.8%) was predicted. See FIG. 4. Additionally, a loss of 3-5 g of scyllitol can be accounted for due to the sampling of each diborate lot.

Preparation of Recovered Diborate

After each isolation of scyllitol, a batch of diborate was recovered from the acidic filtrate by heating the compound to 85-95° C., raising the pH to 9-10 and then cooling it to 20-30° C. In order to optimize the use of equipment for large-scale production, the three filtrates from scyllitol batches 7-9 were combined and used to prepare one batch of recovered diborate, rather than recovering diborate from each of the hydrolysis filtrates separately. For batches 10-13, the recoveries were performed separately.

The five batches of recovered diborate proceeded as expected, by heating the filtrates to 80-90° C. over 1-2 hours, adjusting the pH to 9.0 with caustic, allowing the batches to stir at 80-83° C. for 1 hour, cooling to 20-30° C. over 2.5-4.5 hours (batch from batch 10 was allowed to cool for 14 hours) and agitating at 20-30° C. for 2 hours. Table 6 summarizes the data for the five batches of recovered diborate. Yields ranged from 29 to 35% with HPLC purities of >99.9%. While nickel and aluminum levels increased with each subsequent recovered diborate, the resulting batches of scyllitol continued to have low levels (Table 6).

TABLE 6

Production Summary for Recovered Diborate

| Scyllitol Batch | Recovered Diborate Yield (%)[a] | % H$_2$O | HPLC (% AUC)[b] | Ni and Al (ppm) | $^1$H NMR |
|---|---|---|---|---|---|
| 7 | 718.8 g (33.0%) | 56.1 | >99.9 | Ni: 34, Al: 9 | Consistent |
| 8 | | | | | |
| 9 | | | | | |
| 10 | 203.0 g (30.8%) | 42.6 | >99.9 | Ni: 50, Al: 7 | Consistent |
| 11 | 55.6 g (29.0%) | 35.2 | >99.9 | Ni: 182, Al: 20 | Consistent |
| 12 | 20.7 g (31.0%) | 50.8 | >99.9 | Ni: 510, Al: 61 | Consistent |
| 13 | 5.9 g (35.0%) | 33.9 | >99.9 | Ni: 1526, Al: 204 | Consistent |

[a]Diborate outputs are reported as filter-cake weights with yields that have been corrected for moisture content.
[b]Diborate was analyzed by HPLC.

Without intending to be bound by theory, a possible explanation for the increase in nickel and aluminum levels is based on the solubility of the hydroxide and chloride salts of nickel and aluminum. During the hydrolysis step, the 34 ppm of nickel and 9 ppm of aluminum in the first batch of recovered diborate are converted to the corresponding soluble chlorides which remain in the filtrate, thus yielding acceptable scyllitol. When the acidic filtrate is converted to the subsequent batch of recovered diborate (pH 9-10) the resulting insoluble hydroxide salts of nickel and aluminum are precipitated along with the diborate. With each iteration of this protocol the resulting mass of recovered diborate decreased resulting in increased levels of nickel and aluminum.

This example was designed to represent a worst-case scenario with respect to the potential for contamination due to recycling. While these data indicate that this approach yields scyllitol with acceptable levels of contaminants, recycling conditions can be employed during normal production. Specifically, recovered diborate can be blended with fresh diborate to reduce the amount of residual nickel and aluminum present in the subsequent batch of diborate.

Additional 1/10-Scale Recycling of Diborate Filtrate

In another aspect of the process, recycling of the diborate filtrate was continued ten times on a 1/10 scale after the first five recycles were carried out as described above. The purpose of this exercise was to determine if a failure point could be observed for this recycling protocol. Initially, the quality of these additional diborate batches was simply compared to the batches described above; however, after the initial assessment, the last batch of diborate was carried forward to scyllitol. In principle, this reaction would represent the 15$^{th}$ successful recycle of the diborate filtrate and would drive the diborate yield up to nearly 45%.

Figure 3:
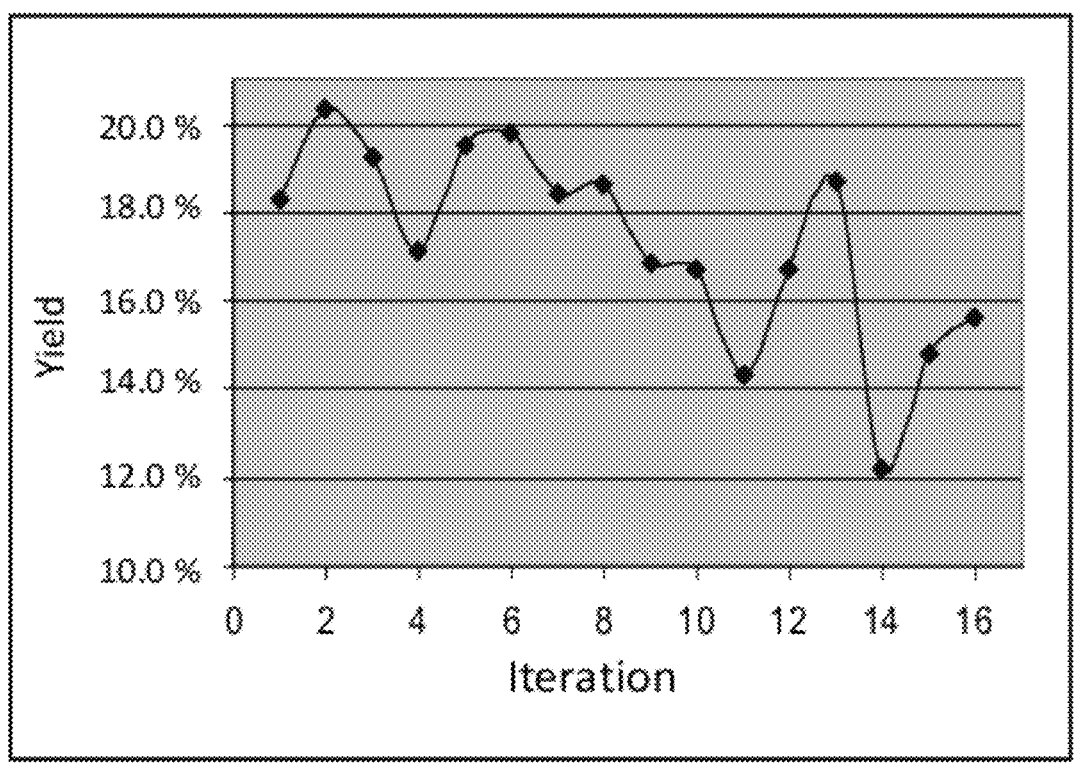
FIG. 3. Scyllitol diborate yield using recycling of inositol recovery mixture as a function of recycling steps.

Ten additional recycles of the diborate filtrate on a 1/10 scale were completed. These reactions proceeded as expected with respect to the isomerization analysis ($^1$H NMR) and diborate formation analysis ($^1$H NMR) and resulted in diborate batches (batches 14-23) with consistent $^1$H NMR spectra and HPLC purities of >99.9%. Table 7 summarizes the data for these experiments. While the quality of diborate after 15 recycles is acceptable, it appears that the fluctuating yield decreased (FIG. 3). The average yield for the first eight reactions and the second eight reactions was 18.9% and 15.7%, respectively. In Table 8 the HPLC profile for each of the 1/10-scale recycles is tabulated. The data indicate that the relative amounts of each component observed in the HPLC was relatively constant.

TABLE 7

Summary for Ten Additional Diborate Filtrate Recycles (1/10 Scale)

| Stage | Batch | Isomerization Analysis ($^1$H NMR) | Product Output (%)[a] | % H$_2$O | HPLC (% AUC) | Ni and Al (ppm) | $^1$H NMR |
|---|---|---|---|---|---|---|---|
| Diborate | 14 | 2.7:1 | 31.69 g (18.4%) | 37.9 | >99.9 | Ni: 7, Al: <1 | Consistent |
| | 15 | 2.0:1 | 31.30 g (18.6%) | 36.5 | >99.9 | Ni: 4, Al: 197 | Consistent |
| | 16 | 2.4:1 | 31.22 g (16.8%) | 42.4 | >99.9 | Ni: 6, Al: <1 | Consistent |
| | 17 | 2.1:1 | 28.00 g (16.7%) | 36.2 | >99.9 | Ni: 9, Al: <1 | Consistent |
| | 18 | 2.9:1 | 25.87 g (14.3%) | 40.8 | >99.9 | Ni: 8, Al: 1 | Consistent |
| | 19 | 2.1:1 | 32.40 g (16.7%) | 45.0 | >99.9 | Ni: 5, Al: 4 | Consistent |
| | 20 | 2.1:1 | 32.85 g (18.7%) | 39.2 | >99.9 | Ni: 8, Al: 2 | Consistent |
| | 21 | 2.6:1 | 28.42 g (12.2%) | 54.2 | >99.9 | Ni: 8, Al: 2 | Consistent |
| | 22 | 2.3:1 | 25.98 g (14.8%) | 39.2 | >99.9 | Ni: 16, Al: 2 | Consistent |
| | 23 | 2.6:1 | 28.57 g (15.6%) | 41.4 | >99.9 | Ni: 8, Al: 1 | Consistent |

[a]Outputs are reported as filter-cake weights and yields are corrected for moisture content.

It was desirable to know that high-quality scyllitol could be obtained from diborate that came from the 15$^{th}$ recycle of diborate filtrate. To this end, batch 22 of diborate was carried forward to scyllitol, and the resulting material (batch 23) met all specifications except for % ROI which was found to be 0.3% (Table 9). Based on this result and the previously mentioned dropping yields it is unlikely that the diborate filtrate will be recycled more than 8-10 times. It was then decided to carry diborate batch 16 (8$^{th}$ recycle) forward to scyllitol (batch 24). Once again the material met all specifications except for % ROI (Table 9). Both samples were resubmitted for ROI and batch 24 was found to have <0.1% ROI and batch 23 was found to have 0.5% ROI. Without intending to be bound by theory, the discrepancy may result from contamination in the sulfuric acid used to digest the samples. Since the available metals analysis revealed low levels of residual metals it was not clear what the source for the high ROI was. ICP analysis on the residue from the ROI analysis did not identify any elements at high enough levels to account for ROI levels of 0.3%-0.5%. While more recycles may be possible, based on this information it is recommended to recycle the diborate filtrate five times.

TABLE 8

HPLC Data for the Additional 1/10-Scale Recycled Diborate Filtrates[a]

| Name | $t_R$ (min) | Batch 14 | Batch 15 | Batch 16 | Batch 17 | Batch 18 | Batch 19 | Batch 20 | Batch 21 | Batch 22 | Batch 23 |
|---|---|---|---|---|---|---|---|---|---|---|---|
| | 6.1 | 0.98 | 1.02 | 1.07 | 0.87 | 0.81 | 0.41 | 0.72 | 0.90 | 0.51 | 0.51 |
| | 7.3 | 0.47 | 0.42 | 0.35 | 0.36 | 0.50 | 0.38 | 0.52 | 0.26 | 0.39 | 0.31 |
| | 8.7 | 0.92 | 0.85 | 0.62 | 0.72 | 0.49 | 0.57 | 0.75 | 0.68 | 0.50 | 0.48 |
| | 9.5 | 9.98 | 9.56 | 8.92 | 7.81 | 6.13 | 6.82 | 7.39 | 6.85 | 6.06 | 5.40 |
| | 10.2 | 5.97 | 5.81 | 5.29 | 4.72 | 3.66 | 4.02 | 4.45 | 4.15 | 3.74 | 3.12 |
| | 13.1 | 0.36 | 0.00 | 0.00 | 0.17 | 0.00 | 0.00 | 0.13 | 0.29 | 0.00 | 0.00 |
| | 13.8 | 0.18 | 0.00 | 0.28 | 0.23 | 0.00 | 0.00 | 0.00 | 0.24 | 0.00 | 0.00 |
| | 14.3 | 0.34 | 0.23 | 0.16 | 0.36 | 0.34 | 0.27 | 0.35 | 0.16 | 0.16 | 0.00 |
| | 15.4 | 0.39 | 0.36 | 0.18 | 0.38 | 0.25 | 0.24 | 0.54 | 0.33 | 0.13 | 0.26 |
| | 16.2 | 0.46 | 0.55 | 0.33 | 0.47 | 0.43 | 0.40 | 0.36 | 0.52 | 0.16 | 0.41 |
| | 18.2 | 0.22 | 0.00 | 0.00 | 0.00 | 0.00 | 0.00 | 0.00 | 0.00 | 0.00 | 0.00 |
| | 18.6 | 1.48 | 1.27 | 1.38 | 0.68 | 0.90 | 0.96 | 1.28 | 0.77 | 0.76 | 0.81 |
| | 19.5 | 1.67 | 1.17 | 1.51 | 0.92 | 0.68 | 1.12 | 0.98 | 0.83 | 0.79 | 0.95 |
| | 20.2 | 2.19 | 1.54 | 1.41 | 0.99 | 0.90 | 1.41 | 1.44 | 1.21 | 1.06 | 0.93 |
| allo-Inositol | 21.5 | 1.04 | 1.34 | 1.17 | 0.84 | 1.10 | 1.39 | 1.14 | 1.40 | 0.68 | 0.98 |
| muco-Inositol | 22.3 | 0.58 | 0.39 | 0.50 | 0.36 | 0.81 | 0.78 | 0.67 | 0.61 | 0.32 | 0.62 |
| | 30.3 | 7.59 | 7.18 | 6.92 | 7.28 | 5.50 | 7.13 | 7.54 | 7.68 | 6.55 | 6.99 |
| chiro-Inositol | 32.3 | 16.33 | 16.25 | 16.39 | 16.20 | 16.05 | 17.37 | 17.30 | 17.32 | 16.74 | 16.13 |
| neo-Inositol | 33.8 | 6.27 | 6.26 | 6.91 | 7.25 | 7.58 | 7.19 | 6.42 | 5.96 | 7.50 | 7.64 |
| myo-Inositol | 42.6 | 42.58 | 45.80 | 46.41 | 49.28 | 53.45 | 49.48 | 48.02 | 49.84 | 53.95 | 54.47 |
| scyllo-Inositol | 44.9 | 0.00 | 0.00 | 0.00 | 0.00 | 0.00 | 0.00 | 0.00 | 0.00 | 0.00 | 0.00 |

[a]Note that the retention times are slightly different than those reported in Table 3; this is due to HPLC method modifications made during analytical method development.

TABLE 9

Scyllitol from 14th and 8th Recycle of the Diborate Filtrate

| Scyllitol Sample | HPLC (% AUC) | % H$_2$O | ROI[a] | Ni, Al, B, Na (ppm) | $^1$H NMR | XRPD |
|---|---|---|---|---|---|---|
| From 14th Recycle | >99.9 | <0.1 | 0.3% (0.5%) | Ni: <1, Al: 2, B: 33, Na: 13 | Consistent | Consistent |
| From 8th Recycle | >99.9 | <0.1 | 0.3% (<0.1%) | Ni: <1, Al: 2, B: 57, Na: 20 | Consistent | Consistent |

[a]Results from resubmitted samples are reported in parentheses.

Hydrolysis Reaction—Analysis by pH

The above-described hydrolysis reactions were analyzed by $^1$H NMR to determine that scyllitol diborate is completely consumed. This analysis always demonstrated that the reaction had gone to completion (even after as little as 10 minutes at 80° C.). Based on these results, it was concluded that the most likely reasons that this reaction would fail would be if hydrochloric acid were undercharged, a basic contamination was added to the reactor, or if scyllitol diborate was overcharged. All of these potential deviations would be accompanied with a higher pH than usual. Analysis of the reaction by measurement of the pH would simplify the process and could reduce the cycle time significantly.

To explore this further an experiment was executed wherein diborate filter cake (batch 15, 15.75 g, 36.5% LOD, 36.3 mmol) was slurried in DI water (90 mL, 9.6 vol) and the slurry was heated to 85-87° C. (pH 9.7). Concentrated HCl was added in 8 aliquots (8×1 mL, 96.5 mmol total); 10-20 minutes after each HCl charge, the reaction pH was recorded and a sample was analyzed by $^1$H NMR (Table 10). After the fourth addition of HCl, the slurry became a solution (pH 5.8) and after the fifth addition of HCl, diborate was not detected by $^1$H NMR (pH 1.1). The pH after the remaining additions of HCl reached 0.5 (typical). Based on these results roughly 60% of the HCl that is typically used for the hydrolysis reaction is required and the reaction goes to completion at a pH of 1.1-5.7. This experiment indicates that the reaction may usefully be monitored by measurement of pH as the reaction progresses.

TABLE 10

Evaluation of pH Method for Analysis of Hydrolysis

| Entry | HCl Charge (Combined) | Hold Time | pH | Results |
|---|---|---|---|---|
| Typical | 2.75 equiv | 1 hour | 0.5 | Complete reaction (solution) |
| 1 | 0.33 equiv | 13 min | 7.5 | Diborate present (slurry) |
| 2 | 0.33 equiv (0.66) | 13 min | 6.7 | Diborate present (slurry) |
| 3 | 0.33 equiv (0.99) | 20 min | 6.3 | Diborate present (slurry) |
| 4 | 0.33 equiv (1.32) | 12 min | 5.8 | Diborate present (solution) |
| 5 | 0.33 equiv (1.65) | 18 min | 1.1 | Complete reaction (solution) |
| 6 | 0.33 equiv (1.98) | 15 min | 0.7 | Complete reaction (solution) |
| 7 | 0.33 equiv (2.31) | 14 min | 0.5 | Complete reaction (solution) |
| 8 | 0.33 equiv (2.64) | 14 min | 0.5 | Complete reaction (solution) |

CONCLUSIONS

The above-described results demonstrate an all-aqueous process for the preparation of scyllitol diborate and scyllitol (6 batches of diborate and 7 batches of scyllitol). This evaluation focused on the recycling of the diborate filtrate (i.e. inositol recovery filtrate into the isomerization reaction), the elimination of a carbon treatment, an all-aqueous isolation of scyllitol and a recovery of diborate from the hydrolysis filtrate. The reactions were primarily executed in 12-L and 22-L, jacketed equipment with extended hold times. The procedures successfully increased the overall yield from 17% to 35% (as predicted based on previous lab experiments). The quality of the scyllitol was comparable to material obtained using standard production procedures. Additionally, the diborate filtrate was further recycled on a 1/10 scale for ten iterations in an effort to find a failure point for recycling this waste stream. This study revealed that diborate filtrate could successfully be recycled five times without having a detrimental effect on the yield or quality of scyllitol. It is possible that additional recycles of the diborate filtrate could be viable. The processes described in these examples have been scaled up for large scale production of scyllitol, resulting in several lots of scyllitol diborate ranging from 188.0 kg to 292 kg, and final material ranging from 87.0 to 108.6 kg of scyllitol with purities no less than 99.9% by HPLC, with boron levels of 11 to 225 ppm, aluminum levels of 0.18 to 0.63 ppm, and nickel levels of 0.27 to 1.4 ppm, demonstrating the methods described herein as suitable for commercial production of scyllitol for pharmaceutical use or for human consumption. These processes can be scaled up further, or batches can be combined to provide efficient and cost-effective production of more than about 500 kg, also about 1000 kg, also about 2000 kg, also about 3000 kg, also about 4000 kg, also about 5000 kg of scyllitol diborate, such as about 1-5000 kg, also about 10-5000 kg, also about 50-5000 kg, also about 50-4000 kg, also about 50-3000 kg, also about 50-2000 kg, also about 50-1000 kg, also about 50-500 kg, also about 50-300 kg of scyllitol diborate; and production of more than about 500 kg, also about 1000 kg, also about 2000 kg, also about 3000 kg, also about 4000 kg, also about 5000 kg of scyllitol. Thus, the methods as described herein are suitable for the commercial production of about 1-5000 kg, also about 10-5000 kg, also about 50-5000 kg, also about 50-4000 kg, also about 50-3000 kg, also about 50-2000 kg, also about 50-1000 kg, also about 50-500 kg, also about 50-200 kg of scyllitol.

Experimental Procedures

All raw materials were used without further purification. All residual metals analyses were contracted out to Robertson Microlit Laboratories Inc. Proton NMR spectra were obtained using a Bruker AV300 at 300 MHz. All other analytical analyses were conducted by Albany Molecular Research, Inc. (Albany, N.Y.).

TABLE 11

Preparation of Scyllitol Diborate (Operations using recycled filtrates are bracketed)

| Step | Operation |
|---|---|
| 1 | Charge 700 g of myo-inositol and 2.1 L of DI water to a 12-L jacketed flask. [Charge 269 g of myo-inositol and 2.1 L of recycled diborate filtrate to a 12-L jacketed flask.] |

TABLE 11-continued

Preparation of Scyllitol Diborate (Operations using recycled filtrates are bracketed)

| Step | Operation |
|---|---|
| 2 | With agitation, add 581 g of sponge nickel (A5000) on a dry basis. |
| 3 | Use 2.1 L of DI water to rinse in the sponge nickel. [Use 2.1 L of recycled diborate filtrate to rinse in the sponge nickel.] |
| 4 | Heat the batch to 95-100° C. |
| 5 | Sample the batch after 1, 2, and 3 hours for $^1$H NMR and HPLC analysis (reaction complete when myo/scyllo ratio is <3:1 by NMR or >20% respectively by HPLC). |
| 6 | Cool the batch to 85-95° C. |
| 7 | Filter the batch through a Celite plug. |
| 8 | Rinse the 12-L reactor and Celite plug with 1.4 L of DI water at 50-60° C. |
| 9 | Transfer the batch into a 22-L, jacketed flask containing 150 g of $Na_2B_4O_7$. [Transfer the batch into a 22-L, jacketed flask containing 100 g of $Na_2B_4O_7$.] |
| 10 | Heat the batch to 80-90° C. over 2-3 hours. |
| 11 | Over 5-10 minutes, charge 110 g of 50% NaOH to raise the pH to 9-10. [Over 5-10 minutes, charge 80 g of 50% NaOH to raise the pH to 9-10.] |
| 12 | Allow the batch to stir for 1 hour at 80-90° C. |
| 13 | Sample the batch for $^1$H NMR (reaction is complete when myo/scyllo ratio is >50:1). |
| 14 | Over 4-16 hours cool the batch to 20-30° C. |
| 15 | Agitate the batch for at least 1 hour at 20-30° C. |
| 16 | Filter the slurry. |
| 17 | Rinse the 22-L reactor with 700 mL of DI water and filter the rinse through the filter cake. |
| 18 | Rinse the 22-L reactor with 700 mL of DI water and filter the rinse through the filter cake. |
| 19 | Condition the filter cake for 30 minutes by pulling air through the cake with vacuum. |
| 20 | Filter the slurry. |
| 21 | Rinse the 22-L reactor with 700 mL of DI water and filter the rinse through the filter cake. |
| 22 | Rinse the 22-L reactor with 700 mL of DI water and filter the rinse through the filter cake. |
| 23 | Condition the filter cake for 30 minutes by pulling air through the cake with vacuum. |
| 24 | The product is obtained as a white crystalline wet cake (≈50% $H_2O$) in 17-20% isolated yield. |
| 25 | The purity of the product is typically 99% by HPLC analysis and the identity is confirmed by $^1$H NMR ($D_2O$). Nickel and aluminum levels were typically <17 ppm and <28 ppm respectively. |

TABLE 12

Preparation of Scyllitol

| Step | Operation |
|---|---|
| 1 | Charge 411 g on a dry basis (383 g $H_2O$) of diborate and 1.68 L of DI Water to a 12-L, jacketed flask. |
| 2 | With agitation, charge 2.06 L of 2N HCl to the batch. |
| 3 | Heat the batch to 85-95° C. over 2-3 hours. |
| 4 | Agitate the batch for at least 10 minutes to obtain a solution. |
| 5 | Sample the batch for $^1$H NMR analysis. The reaction is complete when the diborate is not detected. |
| 6 | Cool the batch to 20-30° C. over 3-4 hours. |
| 7 | Filter the slurry. |
| 8 | Rinse the 12-L reactor with 411 mL of DI water and filter the rinse through the filter cake. |
| 9 | Rinse the 12-L reactor with 411 mL of DI water and filter the rinse through the filter cake. |
| 10 | Condition the filter cake for 30 minutes by pulling air through the cake with vacuum. |
| 11 | Dry the filter cake to a constant weight at 75-80° C. under vacuum (typically <14 h). |
| 12 | The product is obtained as a white crystalline material in 60-65% isolated yield. |
| 13 | The purity of the product is typically >99.8% by HPLC analysis and the identity is confirmed by $^1$H NMR ($D_2O$), IR, DSC, and XRPD. Nickel, aluminum, boron and sodium levels were typically <3 ppm, <5 ppm, <60 ppm and <50 ppm respectively. Moisture levels and ROI were typically <0.1% and 0.0% respectively. |

TABLE 13

Preparation of Recovered Diborate

| Step | Operation |
|---|---|
| 1 | Charge the filtrate and washes from the preparation of scyllitol (≈4 L) to a 22-L, round, jacketed flask. |
| 2 | Heat the batch to 80-90° C. over 2-3 hours. |
| 3 | Over approximately 5 minutes, add 800 g of 50% NaOH to the batch to raise the pH to 9-10. |
| 4 | Agitate the batch for at least 1 hour at 80-90° C. |
| 5 | Sample the batch for $^1$H NMR analysis. The reaction is complete when scyllitol is not detected. |
| 6 | Cool the batch to 20-30° C. over 3-4 hours. |
| 7 | Agitate the batch at 20-30° C. for at least 1 hour. |
| 8 | Filter the slurry. |
| 9 | Rinse the 12-L reactor with 1.2 L of DI water and filter the rinse through the filter cake. |
| 10 | Rinse the 12-L reactor with 1.2 L of DI water and filter the rinse through the filter cake. |
| 11 | Condition the filter cake for 30 minutes by pulling air through the cake with vacuum. |
| 12 | The product is obtained as a white crystalline wet cake (≈50% $H_2O$) in 30-35% isolated yield (relative to diborate charge for the hydrolysis step). |
| 13 | The purity of the product is typically 99% by HPLC analysis and the identity is confirmed by $^1$H NMR ($D_2O$). |

All patents, patent publications, and other published references mentioned herein are hereby incorporated by reference in their entireties as if each had been individually and specifically incorporated by reference herein.

While specific examples have been provided, the above description is illustrative and not restrictive. Any one or more of the features of the previously described embodiments can be combined in any manner with one or more features of any other embodiments in the present invention. Furthermore, many variations of the invention will become apparent to those skilled in the art upon review of the specification. The scope of the invention should, therefore, be determined by reference to the appended claims, along with their full scope of equivalents.

What is claimed is:

1. A method of preparing substantially pure scyllitol comprising the steps of:
   a) subjecting a first mixture comprising myo-inositol to a process that converts at least a portion of the myo-inositol to scyllitol, thereby forming a second mixture;
   b) converting the scyllitol in the second mixture to scyllitol diborate, thereby forming a third mixture;
   c) isolating the scyllitol diborate as a solid from the third mixture to provide isolated scyllitol diborate and a first inositol recovery mixture;
   d) converting the isolated scyllitol diborate to scyllitol, thereby forming a fourth mixture;
   e) isolating the scyllitol as a solid from the fourth mixture to provide isolated substantially pure scyllitol and a first diborate recovery mixture;
   f) combining the first inositol recovery mixture with additional myo-inositol to form a fifth mixture;
   g) repeating steps a) through c) on the fifth mixture to provide additional isolated scyllitol diborate and a second inositol recovery mixture; and
   h) repeating step d) with the additional isolated scyllitol diborate, thereby forming a sixth mixture, and repeating step e) with the sixth mixture to provide additional isolated substantially pure scyllitol and a second diborate recovery mixture.

2. The method of claim 1, wherein steps f) through h) are repeated using the second inositol recovery mixture in step f).

3. The method of claim 1, further comprising the steps of:
   i) reacting the first diborate recovery mixture from step e) to form a recovered scyllitol diborate mixture;
   j) isolating the recovered scyllitol diborate from the recovered scyllitol diborate mixture; and
   k) repeating steps d) and e) with the recovered scyllitol diborate, thereby providing additional isolated substantially pure scyllitol and additional diborate recovery mixture.

4. The method of claim 1, wherein step a) comprises a stereoisomerization process.

5. The method of claim 4, wherein the stereoisomerization process is mediated by a catalyst.

6. The method of claim 5, wherein the catalyst is sponge nickel.

7. The method of claim 6, wherein the stereoisomerization process is performed at a temperature in the range of about 90-100° C.

8. The method of claim 7, wherein the stereoisomerization process is performed in aqueous base.

9. The method of claim 1, wherein step a) comprises a bio-conversion process.

10. The method of claim 8, wherein step b) comprises reaction with sodium tetraborate.

11. The method of claim 10, wherein step b) is performed at a temperature in the range of about 75-95° C.

12. The method of claim 11, wherein the reaction of step b) is performed at a pH in the range of about 8-11.

13. The method of claim 12, wherein step b) comprises precipitating scyllitol diborate in the third mixture.

14. The method of claim 13, wherein step c) comprises filtration.

15. The method of claim 14, wherein step d) comprises a hydrolysis reaction.

16. The method of claim 15, wherein the hydrolysis reaction comprises combining scyllitol diborate with about 8-12 volumes of about 1N acid.

17. The method of claim 16, wherein the 1N acid is 1N HCl.

18. The method of claim 17, wherein the hydrolysis reaction is performed at a temperature in the range of about 75-95° C.

19. The method of claim 18, wherein step d) further comprises precipitating scyllitol in the fourth mixture.

20. The method of claim 19, wherein step e) comprises filtration.

21. The method of claim 3, wherein step i) comprises reaction of the first diborate recovery mixture in a basic aqueous reaction mixture.

22. The method of claim 21, wherein step i) is performed at a temperature in the range of about 80-90° C.

23. The method of claim 22, wherein step i) further comprises precipitation of the recovered scyllitol diborate in the recovered scyllitol diborate mixture.

24. The method of claim 23, wherein step j) comprises filtration.

* * * * *